US011639348B2

(12) United States Patent
Withers et al.

(10) Patent No.: US 11,639,348 B2
(45) Date of Patent: May 2, 2023

(54) COMPOSITIONS AND METHODS FOR NEURAMINIDASE DETECTION AND QUANTIFICATION

(71) Applicant: THE UNIVERSITY OF BRITISH COLUMBIA, Vancouver (CA)

(72) Inventors: Stephen G. Withers, Vancouver (CA); Zhizeng Gao, Vancouver (CA)

(73) Assignee: The University of British Columbia

(*) Notice: Subject to any disclaimer, the term of this patent is extended or adjusted under 35 U.S.C. 154(b) by 0 days.

(21) Appl. No.: 16/257,920

(22) Filed: Jan. 25, 2019

(65) Prior Publication Data

US 2019/0233404 A1    Aug. 1, 2019

Related U.S. Application Data

(60) Provisional application No. 62/622,286, filed on Jan. 26, 2018.

(51) Int. Cl.
| | | |
|---|---|---|
| *G01N 33/68* | (2006.01) | |
| *C07D 407/12* | (2006.01) | |
| *G01N 33/573* | (2006.01) | |
| *G01N 33/58* | (2006.01) | |
| *C12Q 1/34* | (2006.01) | |
| *C12Q 1/04* | (2006.01) | |

(52) U.S. Cl.
CPC .......... *C07D 407/12* (2013.01); *C12Q 1/04* (2013.01); *C12Q 1/34* (2013.01); *G01N 33/573* (2013.01); *G01N 33/582* (2013.01); *G01N 33/6845* (2013.01); *C12Y 302/01018* (2013.01); *G01N 2333/11* (2013.01); *G01N 2333/924* (2013.01)

(58) Field of Classification Search
CPC ............... C07D 407/12; G01N 33/573; G01N 33/582; G01N 33/6845; G01N 2333/924; G01N 2333/11; C12Y 302/01018
USPC ........................................................ 536/18.1
See application file for complete search history.

(56) References Cited

FOREIGN PATENT DOCUMENTS

WO      WO-9109975 A1 *  7/1991

OTHER PUBLICATIONS

Gao et al. (Angew. Chem. Int. Ed. 2017, 56, 6112-6116).*
Gao et al. (Glycobiology vol. 12 No. 3 pp. 183-190, 2002).*
Yolken et al. (J. Infectious Diseases vol. 142, No. 4., 516-523 (1980)).*
Week et al. (Chem. Commun., 2015, 51, 2933-2935).*
Welte et al. (Analytical Biochemistry 338 (2005) 32-38).*
J.-S. Casalegno, O. Ferraris, V. Escuret, M. Bouscambert, C. Bergeron, L. Lines, T. Excoffier, M. Valette, E. Frobert, S. Pillet, et al., PLoS One 2014, 9, e104009.
R. Wagner, M. Matrosovich, H.-D. Klenk, Rev. Med. Virol. 2002, 12, 159-66.
D. J. Benton, S. R. Martin, S. A. Wharton, J. W. McCauley, J. Biol. Chem. 2015, 290, 6516-6521.
M. J. Memoli, P. A. Shaw, A. Han, L. Czajkowski, S. Reed, R. Athota, T. Bristol, S. Fargis, K. Risos, J. H. Powers, et al., MBio 2016, 7, e00417-16.
M. L. Clements, R. F. Betts, E. L. Tierney, B. R. Murphy, J. Clin. Microbiol. 1986, 24, 157-160.
J. L. Virelizier, A. C. Allison, G. C. Schild, Br. Med. Bull. 1979, 35, 65-68.
R. B. Couch, R. L. Atmar, L. M. Franco, J. M. Quades, J. Wells, N. Arden, D. Nio, J. W. Belmont, J. Infect. Dis. 2013, 207, 974-981.
A. S. Monto, J. G. Petrie, R. T. Cross, E. Johnson, M. Liu, W. Zhong, M. Levine, J. M. Katz, S. E. Ohmit, J. Infect. Dis. 2015, 212, 1191-1199.
A. Monto, A. Kendal, Lancet 1973, 301, 623-625.
G. C. Schild, R. W. Newman, J. Hyg. (Lond). 1969, 67, 353-365.
T. J. Wohlbold, F. Krammer, Viruses 2014, 6,2465-2494.
A. Jagadesh, A. A. A. Salam, P. P. Mudgal, G. Arunkumar, Arch. Virol. 2016, 161, 2087-2094.
R. A. Bright, K. M. Neuzil, Y. Pervikov, L. Palkonyay, Vaccine 2009, 27, 6366-6369.
A. A. Ghate, G. M. Air, Eur. J. Biochem. 1998, 258, 320-31.
X. Zhu, R. McBride, C. M. Nycholat, W. Yu, J. C. Paulson, I. a. Wilson, J. Virol. 2012, 86, 13371-13383.
M. Prevato, I. Ferlenghi, A. Bonci, Y. Uematsu, G. Anselmi, F. Giusti, S. Bertholet, F. Legay, J. L. Telford, E. C. Settembre, et al., PLoS One 2015, 10, 1-18.
R. Xu, X. Zhu, R. McBride, C. M. Nycholat, W. Yu, J. C. Paulson, I. A. Wilson, J. Virol. 2012, 86, 9221-32.
P. M. Schmidt, R. M. Attwood, P. G. Mohr, S. A. Barrett, J. L. McKimm-Breschkin, PLoS One 2011, 6, e16284.
H.-L. Yen, C.-H. Liang, C.-Y. Wu, H. L. Forrest, A. Ferguson, K.-T. Choy, J. Jones, D. D.-Y. Wong, P. P.-H. Cheung, C.-H. Hsu, et al., Proc. Natl. Acad. Sci. U. S. A. 2011, 108, 14264-14269.
P. J. Campbell, S. Danzy, C. S. Kyriakis, M. J. Deymier, A. C. Lowen, J. Steel, J. Virol. 2014, 88, 3802-14.
W. Choi, J. Y. Shin, H. E. Jeong, M. J. Jeong, S. J. Kim, J. Y. Lee, C. Kang, Osong Public Heal. Res. Perspect. 2013, 4, 323-328.
H. Yen, N. A. Ilyushina, R. Salomon, R. G. Webster, E. A. Govorkova, E. Hoffmann, J. Virol. 2007, 04, 12418-12426.
J. A. L. Ives, J. A. Carr, D. B. Mendel, C. Y. Tai, R. Lambkin, L. Kelly, J. S. Oxford, F. G. Hayden, N. A. Roberts, Antiviral Res. 2002, 55, 307-317.
P. Simon, B. P. Holder, X. Bouhy, Y. Abed, C. A. A. Beauchemin, G. Boivin, J. Clin. Microbiol. 2011, 49, 715-717.
Y. Abed, A. Pizzorno, X. Bouhy, G. Boivin, Antiviral Res. 2015, 114, 57-61.
M. Z. Wang, C. Y. Tai, D. B. Mendel, Antimicrob. Agents Chemother. 2002, 46, 3809-3816.
D. Blumenkrantz, K. L. Roberts, H. Shelton, S. Lycett, W. S. Barclay, J. Virol. 2013, 87, 10539-51.
N. A. Ilyushina, N. V Bovin, R. G. Webster, J. Virol. 2012, 86, 4724-33.

(Continued)

*Primary Examiner* — Shaojia A Jiang
*Assistant Examiner* — Michael C Henry
(74) *Attorney, Agent, or Firm* — KW Law, LLP

(57) ABSTRACT

Provided herein are compounds having the structure of Formulas A-D and compositions thereof for use in the detection and quantification of viral neuraminidase. In particular, the compounds may be useful for the evaluation of viral strains and for vaccine evaluation.

13 Claims, 9 Drawing Sheets

(56) References Cited

OTHER PUBLICATIONS

A. G. LHuillier, Y. Abed, T. J. Petty, S. Cordey, Y. Thomas, X. Bouhy, M. Schibler, A. Simon, Y. Chaiandon, C. Van Delden, et al., J. Infect. Dis. 2015, 212, 1726-1734.

M. A. Rameix-Welti, F. Agou, P. Buchy, S. Mardy, J. T. Aubin, M. Veron, S. Van Der Werf, N. Naffakh, Antimicrob. Agents Chemother. 2006, 50, 3809-3815.

K. A. Hooper, J. D. Bloom, J. Virol. 2013, 87, 12531-12540.

D. D. Y. Wong, K.-T. Choy, R. W. Y. Chan, S. F. Sia, H.-P. Chiu, P. P. H. Cheung, M. C. W. Chan, J. S. M. Peiris, H.-L. Yen, J. Virol. 2012, 86, 10558-70.

J. Seladi-Schulman, P. J. Campbell, S. Suppiah, J. Steel, A. C. Lowen, PLoS One 2014, 9,1-10.

N. M. Bouvier, S. Rahmat, N. Pica, J. Virol. 2012, 86, 7268-79.

A. Pizzomo, Y. Abed, C. Rheaume, X. Bouhy, G. Boivin, Antimicrob. Agents Chemother. 2013, 57, 1784-1789.

H.-L. Yen, J. L. McKimm-Breschkin, K.-T. Choy, D. D. Y. Wong, P. P. H. Cheung, J. Zhou, I. H. Ng, H. Zhu, R. J. Webby, Y. Guan, et al., MBio 2013, 4, e00396-13-e00396-13.

M. Aymard, Vaccine 2002, 20, 59-60.

T. L. Williams, J. L. Pirkle, J. R. Barr, Vaccine 2012, 30,2475-2482.

M. Getie-Kebtie, I. Sultana, M. Eichelberger, M. Alterman, Influenza Other Respi. Viruses 2013, 7, 521-530.

C. Gravel, C. Li, J. Wang, A. M. Hashem, B. Jaentschke, K. Xu, B. Lorbetskie, G. Gingras, Y. Aubin, G. Van Domselaar, et al., Vaccine 2010, 28, 5774-5784.

J.-H. Kim, R. Resende, T. Wennekes, H.-M. Chen, N. Bance, S. Buchini, a. G. Watts, P. Pilling, V. a. Streltsov, M. Petrie, et al., Science 2013, 71, 71-75.

M. von Itzstein, W.-Y. Y. Wu, G. B. Kok, M. S. Pegg, J. C. Dyason, B. Jin, T. Van Phan, M. L. Smythe, H. F. White, S. W. Oliver, et al., Nature 1993, 363, 418-423.

W. C. Sun, K. R. Gee, R. P. Haugland, Bioorg. Med. Chem. Lett. 1998, 8, 3107-10.

S. Buchini, F. X. Gallat, I. R. Greig, J. H. Kim, S. Wakatsuki, L. M. G. Chavas, S. G. Withers, Angew. Chemie Int. Ed. 2014, 53, 3382-3386.

K. Khazaei, J. H. F. Yeung, M. M. Moore, A. J. Bennet, Can. J. Chem. 2015, 93, 1207-1213.

K. Feichtinger, C. Zapf, H. L. Sings, M. Goodman, J. Org. Chem. 1998, 3263, 3804.

R. Kitz, I. B. Wilson, J. Biol. Chem. 1962, 237, 3245.

Z. Gao, M. Niikura, S. G. Withers, Angew. Chem. Int. Ed. 2017, 56, 6112-6116.

R. W. Myers, R. T. Lee, Y. C. Lee, G. H. Thomas, L.W. Reynolds and Y. Uchida, Analytical Biochemistry, 101, 166-174, (1980).

X-L. Sun, Y. Kanie, C-T. Guo, O. Kanie, Y. Suzuki, and C-H. Wong, Eur. J. Org. Chem., 2643-2653, (2000).

* cited by examiner

FaxOHDFSA, R = OH
FaxAmDFSA, R = ammonium
FaxGuDFSA, R = guanidinium

FaxOHSAF2Mu (1), R = OH
FaxAmSAF2Mu (2), R = ammonium
FaxGuSAF2Mu (3) R = guanidinium

B

Titration Reagents + NA

[Neuraminidase] = [$F_2Mu$]
Neuraminidase concentration ready in 5 min!

(A)

(B)

$k_i$ = 2.9 ± 0.17 min$^{-1}$ $K_i$ = 17.9 ± 2.6 µM $k_i/K_i$ = 18.0 ± 3.83 min$^{-1}$ µM$^{-1}$

COMPOSITIONS AND METHODS FOR NEURAMINIDASE DETECTION AND QUANTIFICATION

CROSS REFERENCE TO RELATED APPLICATIONS

This application claims the benefit of U.S. Provisional Patent Application Ser. No. 62/622,286 filed on 26 Jan. 2018, entitled "NEURAMINIDASE DETECTION AND QUANTITATION".

TECHNICAL FIELD

This invention relates to analytics, their use and methods for the detection of viral components in a sample. In particular, the invention relates to compounds, compositions, analytics, diagnostics, and methods of quantitating neuraminidases.

BACKGROUND

The influenza virus represents a major health burden worldwide both in terms of annual epidemics and occasional global pandemics.[1] Annual global death tolls are estimated at 250,000 to 500,000 while the 2009 H1N1 pandemic resulted in 18,500 laboratory-confirmed deaths, with the real mortality likely being much higher due to the lack of diagnosis.[2] It is known that the influenza virus has two crucial surface glycoproteins, hemagglutinin (HA) and neuraminidase (NA); wherein the virus first attaches to the host cell surface sialic acid, via the HA, triggering endocytosis and entry into the host cell where it replicates,[3] then the influenza NA plays its role in cleaving off the cell surface sialic acids after budding of new virus particles, allowing the virus to escape and infect new cells. Reportedly, the fitness of the influenza virus is highly dependent on the balance of the HA and NA activities.[4-6] It is therefore important to have access to simple and accurate methodologies for measuring the HA and NA parameters in order to understand the infectivity of various strains and resistance development.

Currently, vaccination is still the primary means to manage influenza outbreaks, with approved vaccines focusing on HA activities, e.g. the FDA requires commercial vaccines to contain at least 15 µg of HA from each strain of virus. On the other hand, the important role of NA in the development of an influenza infection has been established.[7-16] NA has been accepted as a major target for the development of anti-influenza drugs and has also attracted increasing attention as a vaccine target due to accumulating evidence that NA-neutralizing antibodies contribute to protection from influenza.[7-16] Recently, it was demonstrated in a human challenge model that the NA inhibition titer (NAI) is actually more predictive of protection and reduced sickness than that of HA.[7] However, no method currently exists to accurately and efficiently measure concentrations of active NA in sample, biological samples, clinical samples, virus samples or other crude mixtures, hampering developments on both fronts. Respectively, there are no guidelines, requirements, or regulations of the NA content in vaccinations at this time, although the WHO has expressed supportive interest.[17]

The content of HA can be measured by single-radial-immunodiffusion,[18] while HA-receptor affinity is determined using glycan microarray-based assays.[19-21] However, measurement of absolute kinetic parameters for NA within whole virus samples has not been possible, because reliable and convenient techniques for measuring the concentration of active NA in such samples are currently not available. Nowadays, assays usually use the fluorogenic substrate 4-methylumbelliferyl α-D-N-acetylneuraminide (4-MU-NANA), but absolute kinetic parameters have only been reported for the purified enzymes, which are not easily accessed.[22-26] The 4-MU-NANA substrate can also be used to detect NA activity in samples of virus, but ignorance of the NA concentration therein means that full kinetic parameters cannot be measured.[27-44] Earlier, attempts to quantify the total NA protein have used MS methodologies or specific antibodies,[7-16,45-48] but such methods are cumbersome and measure the total, not the active, amount of enzyme.

There is therefore an urgent need for the development of a general, convenient method to quantify active NA content in samples, both for studying emerging influenza strains and for understanding the contribution of NA to influenza vaccine effectiveness. Furthermore, reagents of this class may also be useful for quantitating other sialidases.

SUMMARY

The present invention is based in part, on the surprising discovery that the compounds described herein are useful for the detection and quantification of viral neuraminidase. In particular, the compounds may be useful for the quantification of viral neuraminidase in the characterization of viral strains and for vaccine preparation and development.

The invention described herein is based in part of the demonstration that one of the best methods for accurately measuring concentrations of specific enzymes, even in complex mixtures, may be through use of an active site titration agent.[49] These may be reagents that react stoichiometrically with the target enzyme and generate a defined change in absorbance or fluorescence of the solution without the need for any separation of reagents. For enzymes that may operate through a covalent intermediate this may be commonly achieved by using a chromogenic substrate for which the second chemical step may be rate-limiting, preferably with a rate constant approaching zero. For example, the 2,3-difluorosialic acids (DFSAs) are known as a class of specific, mechanism-based NA inhibitors, which show promise as anti-influenza therapeutics both in cell-based and animal studies.[50, 53] The invention described herein is further based on the observation that fluorinated sialic acids can function as quite slow substrates for which the second step ($k_{hydr}$) may be quite slow and that in fluorinated sialic acids a sufficiently activated chromogenic or fluorogenic leaving group may be added onto the six-membered ring, e.g. in place of a fluoride leaving group. Wherein such chromogenic or fluorogenic leaving group may need to be a sufficiently good leaving group to undergo enzymatic displacement in a reasonable timescale for analysis. Typically, such chromogenic or fluorogenic leaving group may comprise a phenol moiety. Furthermore, the chromogenic and fluorogenic leaving group may depart from the anomeric center after binding to the enzyme active site; wherein the pKa of the liberated phenol moiety may be less than pKa 10 and preferably less than pKa 6. The fluorinated sialic acids may find wide application in influenza science, especially for the measurement of concentrations of active NA.

In a first embodiment there is provided a compound having the structure of Formula A or a salt thereof,

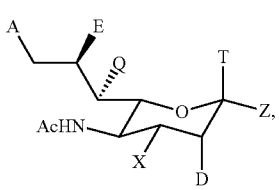

Formula A wherein, T may be selected from COOH, COO⁻ and COOR¹; R¹ may be a $C_{1-20}$ linear, branched or cyclic, saturated or unsaturated, unsubstituted alkyl group; D may be selected from H, F and Cl; X may be selected from OH, N₃, OAc, NH₂, —NHC(NH)NH₂ and —NHC(NBoc)NH-Boc; Q may be selected from H, OH and —O—$(CH_2)_n$—R²; R² may be a $C_{1-20}$ linear, branched or cyclic, saturated or unsaturated, unsubstituted alkyl group; n may be 2, 3, 4 or 5; E may be selected from H, OH,—O—$(CH_2)_n$—R² and OAc; A may be selected from H, OH,—O—$(CH_2)_n$—R² and OAc; and Z may be a chromogenic or fluorogenic group that exhibits a distinct colour and/or fluorescence when cleaved from the substrate or salts of said substrate.

Z may have the structure of Formula B or Formula C:

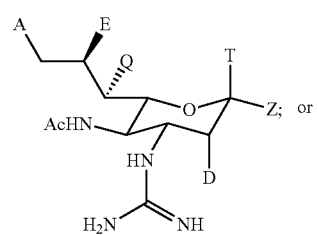

Formula B wherein, L¹ may be O, S or N; M¹ may be O, S or N; M² may be O or S; G¹ may be H, F, Cl, Br or I; G² may be H, CH₃, F, Cl, Br or I; G³ may be H, CH₃, CF₃, F, Cl, Br or I; and G⁴ may be H, CF₃, F, Cl, Br or I; or

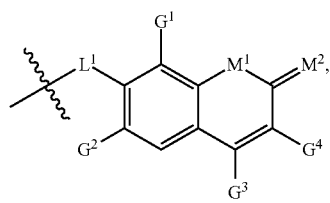

Formula C wherein, L² may be O or S; G¹ may be F or Cl; G² may be H, CH₃, F or Cl; and G⁴ may be H, CF₃.

T may be COOH or COO⁻. T may be COOH. D may be H, F or Cl. D may be F or Cl. D may be F. X may be OH, N₃, OAc, NH₂ or —NHC(NH)NH₂. X may be OH, OAc, NH₂ or —NHC(NH)NH₂. X may be OAc, NH₂ or —NHC(NH)NH₂. X may be NH₂ or —NHC(NH)NH₂. X may be —NHC(NH)NH₂. X may be OH. X may be OAc. X may be NH₂. Q may be H, OH or —O—$(CH_2)_n$—R². Q may be OH or —O—$(CH_2)_n$—R². Q may be —O—$(CH_2)_n$—R². Q may be a $C_{1-6}$ linear or branched saturated or unsaturated, unsubstituted alkyl group. R² may be a $C_{1-10}$ linear or branched saturated or unsaturated, unsubstituted alkyl group. R² may be a $C_{1-20}$ linear or branched saturated or unsaturated, unsubstituted alkyl group. n may be 2, 3, 4 or 5. n may be 2, 3 or 4. n may be 2 or 3. n may be 3 or 4. n may be 2. n may be 3. n may be 4. E may be H, OH,—O—$(CH_2)_n$—R² or OAc. E may be OH,—O—$(CH_2)_n$—R² or OAc. E may be H, OH, or OAc. E may be OH or OAc. E may be OH. A may be H, OH,—O—$(CH_2)_n$—R² or OAc. A may be OH,—O—$(CH_2)_n$—R² or OAc. A may be OH or —O—$(CH_2)_n$—R². A may be OH or OAc. A may be OH.

The compound may have the structure of:

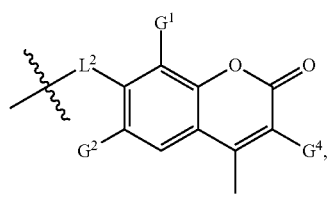

Formula D

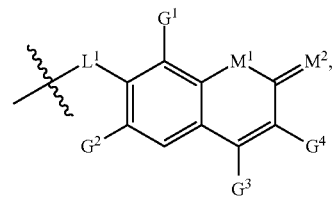

Formula E

Z may have the structure of Formula B:

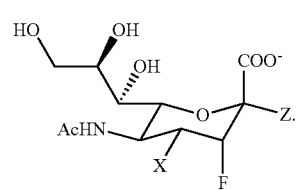

Formula B wherein, L¹ may be O, S or N; M¹ may be O, S or N; M² may be O or S; G¹ may be H, F, Cl, Br or I; G² may be H, CH₃, F, Cl, Br or I; G³ may be H, CH₃, CF₃, F, Cl, Br or I; and G⁴ may be H, CF₃, F, Cl, Br or I. L¹ may be O or S; M¹ may be O or S; M² may be O or S; G¹ may be H, F, Cl or Br; G² may be H, CH₃, F, Cl or Br; G³ may be H, CH₃, CF₃, F, Cl or Br; and G⁴ may be H, CF₃, F, Cl or Br. L¹ may be O. M¹ may be O. M² may be O. G¹ may be H, F, Cl or Br. G² may be H, CH₃, F, Cl or Br. G³ may be H, CH₃, CF₃, F, Cl or Br. G⁴ may be H, CF₃, F, Cl or Br. G¹ may be H, F or Cl. G² may be H, CH₃, F or Cl. G³ may be H, CH₃, CF₃, F or Cl. G⁴ may be H, CF₃, F or Cl. L¹ may be S. M¹ may be S. M² may be S. L¹ may be N. M¹ may be N.

Z may have the structure of Formula C:
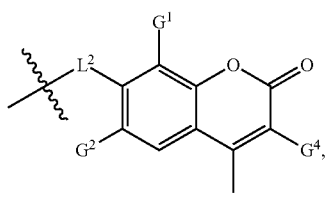
Formula C
wherein,
L² may be O or S; G¹ may be F or Cl; G² may be H, CH₃, F or Cl; and G⁴ may be H, CF₃. L² may be O; G¹ may be F or Cl; G² may be H, CH₃, F or Cl; and G⁴ may be H L² may be O. G¹ may be F or Cl. G² may be H, CH₃, F or Cl. G⁴ may be H or CF₃. L² may be S. G¹ may be Cl. G² may be Cl. G⁴ may be CF₃. G¹ may be F. G² may be F. G² may be CH₃. G² may be H.
Z may be selected from
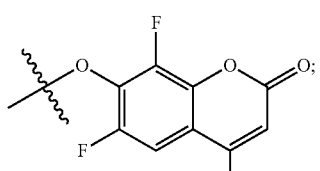
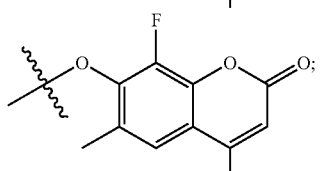
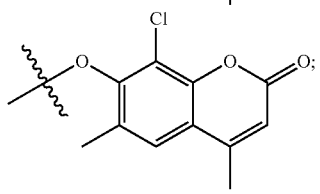
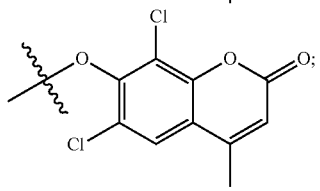
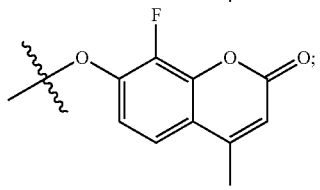
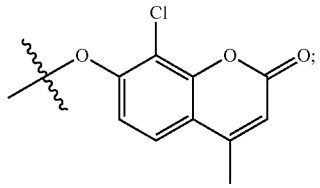
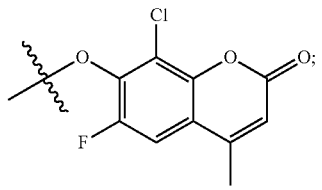
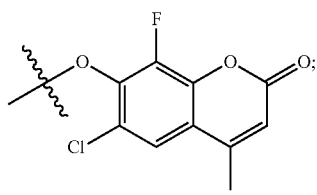
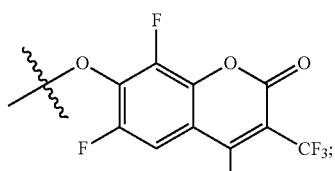
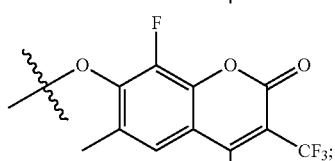
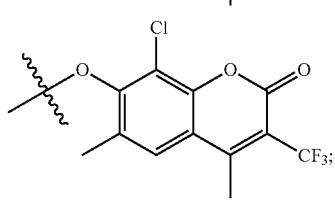
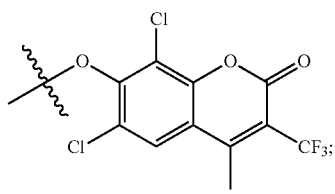
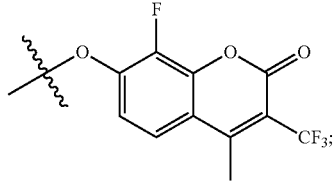
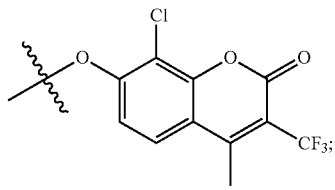
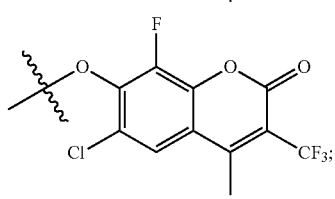

-continued
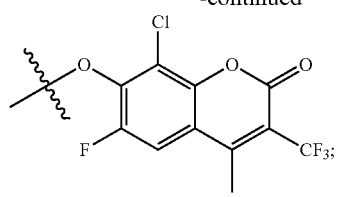
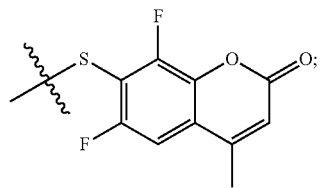
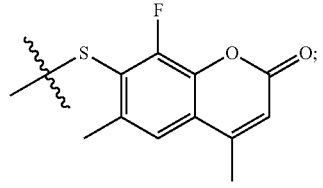
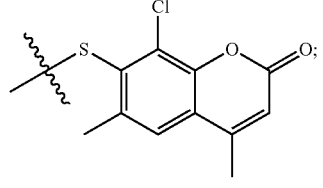
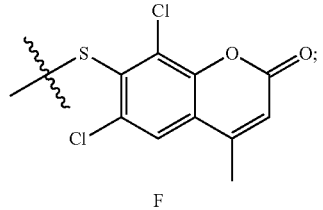
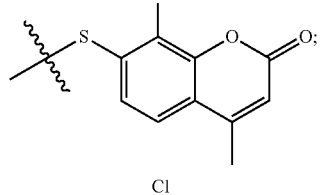
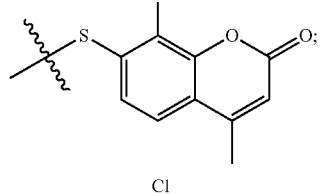
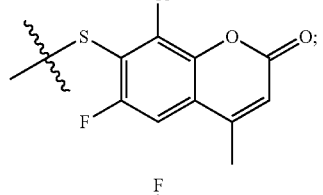
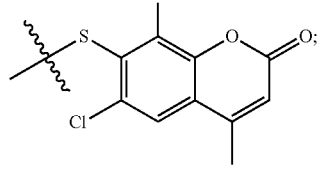
-continued
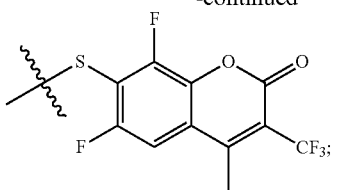
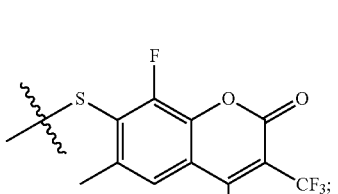
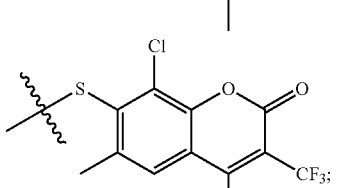
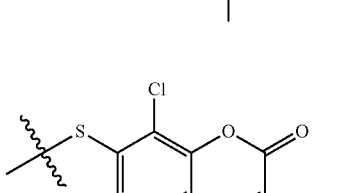
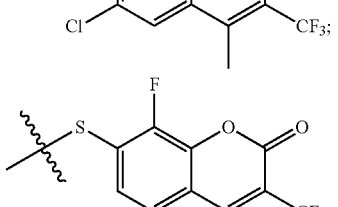
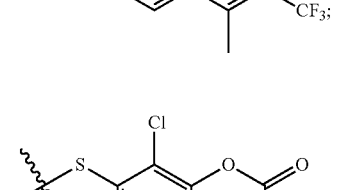
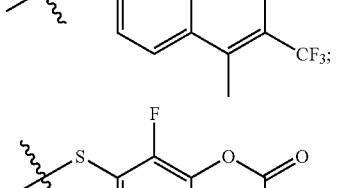
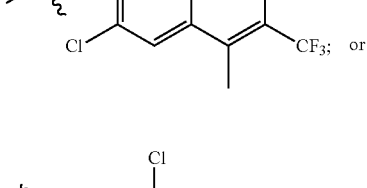 or
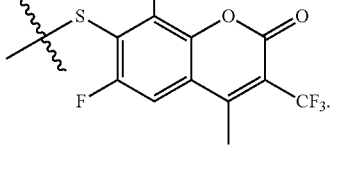

The compound may be selected from one or more of:

[Chemical structure 1: FaxOHSAF2Mu - Neu5Ac derivative with fluorinated methylumbelliferone]

[Chemical structure 2: FaxAmF2Mu - analog with H₂N group]

[Chemical structure 3: peracetylated derivative with CO₂Me]

[Chemical structure 4: peracetylated derivative with N₃ group and CO₂Me]

[Chemical structure 5: peracetylated derivative with BocHN-C(=NBoc)-NH- group and CO₂Me]; and

[Chemical structure 6: FaxGuF2Mu - with H₂N-C(=NH)-NH- guanidino group]

In a further embodiment there is provided a method of detecting a neuraminidase activity in a sample, the method comprising: (a) contacting a sample suspected of having the neuraminidase activity with a compound of claim 1; and (b) detecting a reaction product, wherein exposure of the neuraminidase activity to the compound results in the release of a detectable reaction product.

The detectable reaction product may exhibit a colour or fluorescence. The detectable reaction product may be released in stoichiometric amounts or in a stoichiometric ratio of neuraminidase to reaction product of 1:1. The detectable reaction product may be quantified. The detectable reaction product may be quantified to determine the amount and/or activity of neuraminidase in the sample. The detectable reaction product may be quantified with the aid of a calibration curve or a standardized sample or standardized samples. The neuraminidase activity may be human influenza neuraminidase activity. The neuraminidase activity may be human influenza A neuraminidase activity and/or human influenza B neuraminidase activity. The neuraminidase activity may be bacterial neuraminidase activity. The neuraminidase activity may be non-viral neuraminidase. The sample may be a crude sample, a biological or a clinical sample. The sample may include viral particles or a vaccine. The sample may include a surfactant, a detergent, NP40 and/or ß-propiolactone. The fluorogenic substrate may react with neuraminidase releasing a fluorescent compound, said compound having the formula:

[Chemical structure: F₂Mu - difluoromethylumbelliferone anion];

and wherein the fluorescence emitted from the released compound may be detected and used to calculate the activity of human influenza neuraminidase in the sample. The excitation and emission wavelengths may be 353 nm and 451 nm.

In a further embodiment there is provided a method for making a compound of Formula A as described herein.

Throughout this specification, unless the context requires otherwise, the words "comprise", "comprising" and the like, are to be construed in an inclusive sense as opposed to an exclusive sense, that is to say, in the sense of "including, but not limited to".

BRIEF DESCRIPTION OF THE DRAWINGS

FIG. 1 shows (A) the structures of DFSAs and titration reagents: FaxOHSAF2Mu (1), FaxAmF2Mu (2) and FaxGuF2Mu (3); and (B) the mechanism of action of the titration reagents.

FIG. 2 shows the mechanism of action enables a direct quantification due to 1:1 ratio of one neuraminidase molecule per molecule of F₂Mu released.

DETAILED DESCRIPTION

Figure 3:
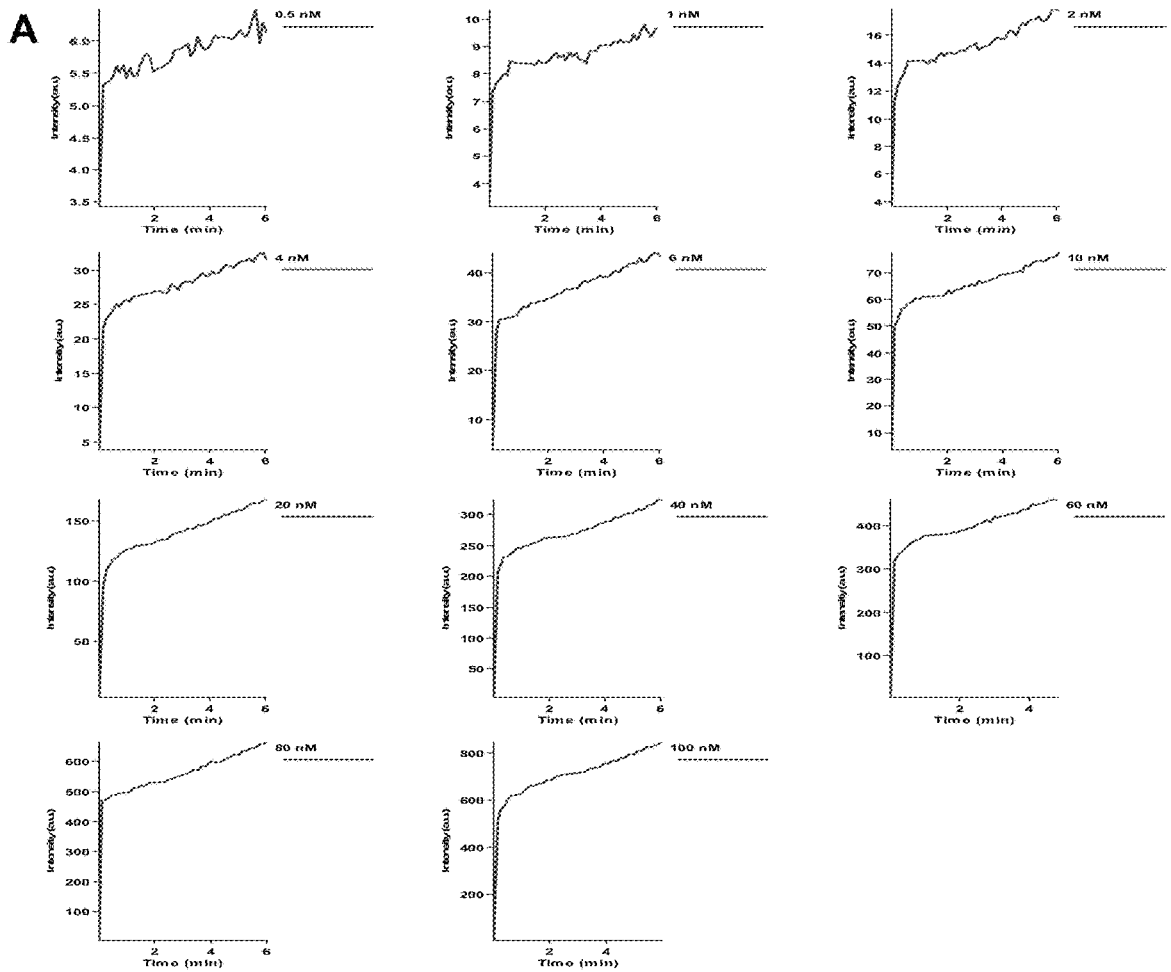
FIG. 3 shows a (A) titration of various concentration of NedA with 1, wherein the release of F₂Mu was monitored fluorimetrically (Ex 353 nm, Em 451 nm), wherein the steady state signal was extrapolated back to the y-axis to get the corresponding burst amplitude; and shows a (B) correlation of the concentrations of NedA calculated based on $A^{280}$ with F₂Mu released: inset shows an expansion of the lowest concentration range.
Figure 3:
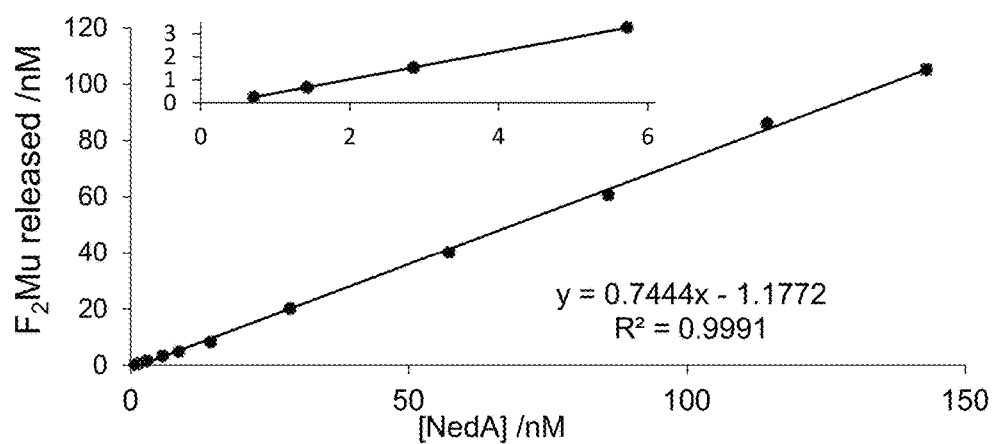

The following detailed description will be better understood when read in conjunction with the appended figures. For the purpose of illustrating the invention, the figures demonstrate embodiments of the present invention. However, the invention is not limited to the precise arrangements and examples shown.

Any terms directly defined herein shall be understood to have the meanings commonly associated with them as understood within the art of the invention.

The abbreviation OAc as used herein refers to an Acetoxy group, which is chemical functional group of the structure CH$_3$—C(=O)—O—.

The abbreviation "Boc" as used herein refers to a tert-butyloxycarbonyl protecting group or a tert-butoxycarbonyl protecting group or BOC group, which is a protecting group used in organic synthesis having the structure

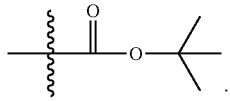 [SMILES: *C(=O)OC(C)(C)C]

The term "influenza" as used herein refers to an infectious disease cause by the influenza virus, commonly known as the flu.

The term "hemagglutinin" or HA as used herein refers to a glycoprotein on the surface of an influenza virus.

The term "neuraminidase" or NA as used herein refers to a glycoside hydrolase enzymes that cleaves the glycosidic linkages of neuraminic acids. A "viral neuraminidase" as used herein refers to a type of neuraminidase found on the surface of a virus, for example an influenza virus.

The term "human influenza A neuraminidase activity" as used herein refers to the enzyme activity found on influenza viruses of Type A that cleaves neuraminic acid from host cells.

The term "human influenza B neuraminidase activity" as used herein refers to the enzyme activity found on influenza viruses of Type B that cleaves neuraminic acid from host cells.

The term "parainfluenza neuraminidase activity" as used herein refers to the enzyme activity found on para-influenza viruses that cleaves neuraminic acid from host cells.

The term "difluorosialic acid" or DFSA as used herein refers to a class of specific, mechanism-based NA inhibitors.

The term "FaxOHSAF$_2$Mu" as used herein refers to 5-Acetamido-3-fluoro-3,4,5-trideoxy-2α-(4-methyl-6,8-difluoromethylumbelliferyl)-D-glycero-D-galactononulopyranosylnoic acid comprising a compound having the Formula 1:

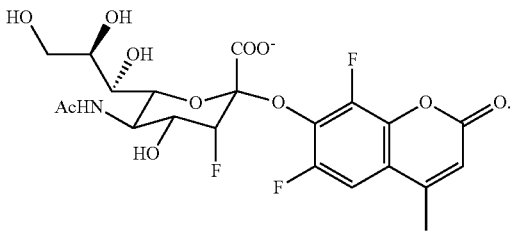

The term "FaxAmSAF$_2$Mu" as used herein refers to 5-Acetamido-4-amino-3-fluoro-3,4,5-trideoxy-2α-(4-methyl-6,8-difluoromethylumbelliferyl)-D-glycero-D-galactononulopyranosylnoic acid comprising a compound having the Formula 2:

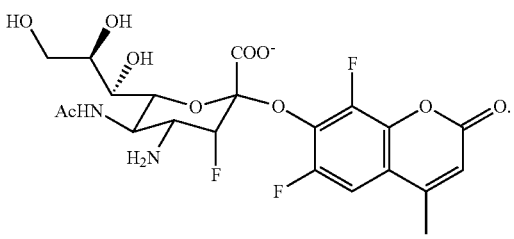

The term "FaxGuSAF$_2$Mu" as used herein refers to 5-Acetamido-4-guanidine-3-fluoro-3,4,5-trideoxy-2α-(4-methyl-6,8-difluoromethylumbelliferyl)-D-glycero-D-galactononulopyranosylnoic acid comprising a compound having the Formula 3:

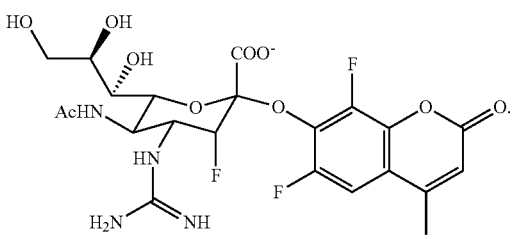

The term "F$_2$Mu" as used herein refers to 6,8-difluorocoumarin comprising a compound having the general chemical structure of

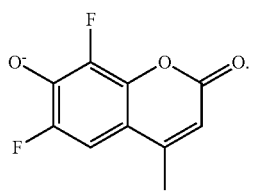

As used herein, a "subject" may be a human, non-human primate, rat, mouse, cow, horse, pig, sheep, goat, dog, cat, beaver, etc. The subject may be suspected of having or at risk for having a viral infection, such as an influenza infection.

The term "biological sample" as used herein refers to a sample derived from sources other than human beings.

The term "clinical sample" as used herein refers to a sample derived from the human body.

The term "vaccine" as used herein refers to a substance administered to a subject to stimulate the production of antibodies (i.e. to act as an antigen) and provide immunity against one or more diseases or infections. The antigen acts as a substitute for a disease particle or an infectious particle to stimulate an immune response without inducing the disease or infection. For example, a vaccine may include an attenuated virus or viral particles that are unable or ineffective at causing infection.

The term "NP40" as used herein refers to nonyl phenoxypolyethoxylethanol.

The term "chromogenic" as used herein refers to "a chromogen", wherein a chromogen is a substance that may be converted into a colored compound or a dye.

The term "fluorescent" is used herein refers to a substance having or showing fluorescence.

The term "fluorogenic group" as used herein refers to a non-fluorescent group that reacts to a fluorescent group.

Compounds as described herein may be in the free form or in the form of a salt thereof. In some embodiment, compounds as described herein may be in the form of a pharmaceutically acceptable salt, which are known in the art (Berge S. M. et al., J. Pharm. Sci. (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formulas illustrated for the sake of convenience.

Various alternative embodiments and examples are described herein. These embodiments and examples are illustrative and should not be construed as limiting the scope of the invention.

Materials and Methods

The procedures described herein are given for the purposes of example and illustration only and should not be considered to limit the spirit or scope of the invention.

General Synthetic Procedures

All reactions involving air or moisture sensitive reactants were conducted under a positive pressure of dry argon. All solvents and chemicals were reagent grade and used as supplied unless otherwise stated. For anhydrous reactions, solvents were dried according to the procedures detailed in Perrin and Armarego[2]. Removal of solvent was performed under reduced pressure, below 40° C., using a Büchi rotary evaporator. All other chemical reagents were purchased from Sigma-Aldrich Chemical Company™. All reactions and fractions from column chromatography were monitored by thin layer chromatography (TLC). Analytical TLC was done on glass plates (5×1.5 cm) pre-coated (0.25 mm) with silica gel (normal $SiO_2$, Merck 60 F254™). Compounds were visualized by exposure to UV light and by dipping the plates in 1% $Ce(SO_4)_2.4H_2O$ 2.5% $(NH_4)Mo_7O_{24}.4H_2O$ in 10% $H_2SO_4$ followed by heating on a hot plate. Flash chromatography was performed on silica gel (EM Science™, 60 Å, 230-400 mesh). The nuclear magnetic resonance (NMR) spectra were either recorded on a Bruker AV-600™ (600 MHZ, with Cryoprobe™), Bruker AV-400™ (400 MHz) or a Bruker AV-300™ (300 MHz) spectrometer. Mass spectra (MS) were recorded by using a Waters/Micromass instrument (electrospray ionization, EI) and recorded using an ion-trap.

Synthesis of methyl 5-acetamido-4,7,8,9-tetra-O-acetyl-3-fluoro-3,5-dideoxy-2α-(4-methyl-6,8-difluoromethylumbelliferyl)-D-glycero-D-galactononulopyranosonate (5)

To a stirred solution of compound 4 (150 mg, 0.29 mmol) in dry THF (5 mL) was added $PPh_3$ (400 mg, 1.52 mmol) and $F_2Mu$ (150 mg, 0.70 mmol) at 25° C. under Ar. Diisopropyl azodicarboxylate (DIED) (0.3 mL, 1.52 mmol) was added dropwise. The reaction was stirred for 12 h. The reaction was quenched by the addition of 10 mL water. 10 mL of EtOAc was added and the layers were separated and the aqueous layer was extracted with EtOAc (3×10 mL). The combined organic layers were washed with brine (20 mL) and dried over $Na_2SO_4$. The solvent was removed under vacuum and the residue was purified using flash column chromatography (10:10:1:0.1 EtOAc/petroleum ether/ MeOH/AcOH) to give 5 as a slightly yellow solid (39 mg, 19%). Recorded NMR spectra (not shown). $^1H$ NMR (400 MHz, Chloroform-d) δ 7.14 (dd, J=10.0, 2.2 Hz, 1H, $F_2Mu$), 6.35 (d, J=1.5 Hz, 1H, $F_2Mu$), 5.50 (d, J=8.9 Hz, 1H, NH), 5.47-5.29 (m, 2H, H-3, H-4), 5.22 (dd, J=8.6, 1.8 Hz, 1H, H-7), 4.87 (ddd, J=8.4, 5.6, 2.6 Hz, 1H, H-8), 4.21 (dd, J=10.8, 1.7 Hz, 1H, H-6), 4.16-4.06 (m, 2H, H-5, H-9), 3.93 (s, 3H, OMe), 3.92-3.85 (m, 1H, H-9), 2.43 (d, J=1.3 Hz, 3H, $F_2Mu$), 2.19 (s, 3H), 2.14 (s, 3H), 1.92 (s, 3H), 1.92 (s, 3H), 1.91 (s, 3H). $^{13}C$ NMR (101 MHz, Chloroform-d) δ 170.9, 170.6, 170.5, 170.5, 169.4, 164.5 (d, J=3.0 Hz), 159.3, 153.0 (dd, J=248.7, 2.4 Hz), 151.6 (t, J=2.4 Hz), 145.0 (dd, J=256.3, 4.4 Hz), 139.4 (dd, J=10.6, 2.7 Hz), 131.2 (dd, J=17.4, 12.5 Hz), 118.5 (d, J=8.7 Hz), 116.2, 105.8 (dd, J=22.5, 3.8 Hz), 99.4 (d, J=16.3 Hz), 86.7 (d, J=195.7 Hz), 72.2, 68.9 (d, J=17.6 Hz), 68.3, 67.4, 62.1, 53.9, 45.6 (d, J=3.8 Hz), 23.5, 20.9, 20.9, 20.8, 20.8, 19.0. $^{19}F$ NMR (282 MHz, $CDCl_3$) δ -128.3, -141.8, -216.4. HRMS (ESI) m/z: Calcd. for $C_{30}H_{32}F_3NO_{15}$ ([M+Na]$^+$): 726.1622; found: 726.1630.

Synthesis of 5-Acetamido-3-fluoro-3,5-dideoxy-2α-(4-methyl-6,8-difluoromethylumbelli-feryl)-D-glycero-D-galactononulopyranosylnoic Acid (1)

To a stirred solution of compound 5 (12 mg, 17 μmmol) in dry MeOH (3 mL) was added a small piece of sodium at 25° C. under Ar. The reaction was stirred for 10 min. AcOH was added to quench the reaction. The solvent was removed under vacuum and the resulting residue was redissolved in water (1.0 mL). THF (3.0 mL) and 0.5 M NaOH (1.5 mL) was added and the resulting solution was stirred for 15 min. AcOH was added to neutralize the solution. The solvent was removed under vacuum and the residue was purified using flash column chromatography (8:2:1 EtOAc/MeOH/Water) to give 1 as a white solid (6.5 mg, 72%). Recorded NMR spectra (not shown). $^1H$ NMR (600 MHz, Methanol-$d_4$) δ 7.35 (dd, J=10.2, 1.9 Hz, 1H, $F_2Mu$), 6.37 (d, J=1.5 Hz, 1H, $F_2Mu$), 5.45 (dd, J=52.2, 2.2 Hz, 1H, H-3), 4.17 (t, J=10.6 Hz, 1H, H-5), 3.98 (ddd, J=28.2, 10.6, 2.2 Hz, 1H, H-4), 3.82 (ddd, J=9.1, 5.3, 2.6 Hz, 1H, H-8), 3.77 (dd, J=11.4, 2.6 Hz, 1H, H-9), 3.62-3.58 (m, 1H, H-9), 3.53-3.47 (m, 2H, H-6, H-7), 2.43 (d, J=1.4 Hz, 3H, $F_2Mu$), 2.00 (s, 3H). $^{13}C$ NMR (101 MHz, Deuterium Oxide) δ 175.21, 168.51 (d, J=3.2 Hz), 162.42, 154.94, 152.88 (dd, J=246.8, 2.7 Hz), 144.3 (dd, J=255.2, 4.6 Hz), 132.52 (dd, J=17.7, 12.5 Hz), 118.34 (d, J=9.4 Hz), 114.72, 106.39 (d, J=22.9 Hz), 102.72 (d, J=13.2 Hz), 90.92 (d, J=184.4 Hz), 73.49, 71.84, 69.74 (d, J=18.3 Hz), 67.95, 62.54, 46.74, 22.12, 18.12. $^{19}F$ NMR (282 MHz, Methanol-$d_4$) δ -127.6, -143.0, -219.1. HRMS (ESI) m/z: Calcd. for $C_{21}H_{21}F_3NO_{11}$ ([M−H]$^-$): 520.1067; found: 520.1075.

Synthesis of methyl 5-acetamido-7,8,9-tri-O-acetyl-4-azido-3-fluoro-3,4,5-trideoxy-2α-(4-methyl-6,8-difluoromethylumbelliferyl)-D-glycero-D-galactononulopyranosonate (7)

To a stirred solution of compound 6 (150 mg, 0.30 mmol) in dry THF (5.0 mL) was added $PPh_3$ (400 mg, 1.52 mmol) and $F_2Mu$ (150 mg, 0.70 mmol) at 25° C. under Ar. Diisopropyl azodicarboxylate (DIED) (0.30 mL, 1.52 mmol) was added dropwise. The reaction was stirred for 12 h. The reaction was quenched by the addition of 10 mL water. 10 mL of EtOAc was added and the layers were separated and the aqueous layer was extracted with EtOAc (3×10 mL). The combined organic layers were washed with brine (20 mL) and dried over $Na_2SO_4$. The solvent was removed under vacuum and the residue was purified using flash column chromatography (10:10:1:0.1 EtOAc/petroleum ether/

MeOH/AcOH) to give 7 as a slightly yellow solid (115 mg, 56%). Recorded NMR spectra (not shown). $^1$H NMR (300 MHz, Chloroform-d) δ 7.12 (dd, J=10.1, 2.2 Hz, 1H, F$_2$MU), 6.33 (d, J=1.5 Hz, 1H, F$_2$MU), 6.15 (d, J=7.6 Hz, 1H, NH), 5.40 (dd, J=50.4, 1.9 Hz, 1H, H-3), 5.21 (dd, J=8.6, 1.5 Hz, 1H, H-7), 4.86 (ddd, J=8.2, 5.2, 2.5 Hz, 1H, H-8), 4.47 (dd, J=28.9, 10.9 Hz, 1H, H-4), 4.34 (d, J=10.7 Hz, 1H, H-6), 4.11-4.04 (m, 1H, H-9), 3.95 (dd, J=12.5, 5.3 Hz, 1H, H-9), 3.89 (s, 3H, OMe), 3.58-3.44 (m, 1H, H-5), 2.41 (d, J=1.3 Hz, 3H, F$_2$MU), 2.18 (s, 3H), 2.02 (s, 3H), 2.00 (s, 3H), 1.91 (s, 3H), 1.90 (s, 3H). $^{13}$C NMR (75 MHz, CDCl$_3$) δ 171.7, 171.5, 170.4, 169.3, 164.3 (d, J=3.4 Hz), 159.3, 152.9 (dd, J=248.7, 1.9 Hz), 151.6 (t, J=2.3 Hz) 145.0 (d, J=260.5 Hz), 139.4 (dd, J=10.5, 2.5 Hz), 131.1 (dd, J=17.4, 12.5 Hz), 118.5 (d, J=8.9 Hz), 116.2, 105.7 (dd, J=22.5, 3.5 Hz), 99.2 (d, J=16.1 Hz, C2), 87.6 (d, J=195.3 Hz, C3). 71.2, 68.2, 67.8, 61.9, 57.4 (d, J=17.3 Hz, C4), 53.9, 47.7, 23.6, 20.9, 20.8, 20.7, 18.9. $^{19}$F NMR (282 MHz, Chloroform-d) δ −128.6, −141.8, −216.0. HRMS (ESI) m/z: Calcd. For C$_{28}$H$_{29}$F$_3$N$_4$O$_{13}$ ([M+Na]+): 709.1581; found: 709.1572.

Synthesis of 5-acetamido-4-amino-3-fluoro-3,4,5-trideoxy-2α-(4-methyl-6,8-difluoromethyl-umbelliferyl)-D-glycero-D-galactononulopyranosylnoic acid (2)

To a stirred solution of compound 7 (20 mg, 29 μmmol) in dry MeOH (3 mL) was added a small piece of sodium at 25° C. under Ar. The reaction was stirred for 10 min. AcOH was added to quench the reaction. The solvent was removed under vacuum and the resulting residue was redissolved in water (1.0 mL). THF (3.0 mL) and 0.5 M NaOH (1.5 mL) was added and the resulting solution was stirred for 15 min. AcOH was added to neutralize the solution. The solution was concentrated down and redissolved in MeOH (2 mL). Lindlar catalyst (2 mg) was added and the resulting solution was stirred under H$_2$ atmosphere for 12 h. The solution was filtered through a short pad of celite and washed with MeOH. The solvent was removed under vacuum and the residue was purified using flash column chromatography (7:2:1 EtOAc/MeOH/Water) to give compound 2 as a white solid (7.6 mg, 50%). Recorded NMR spectra (not shown). $^1$H NMR (400 MHz, Methanol-d$_4$) δ 7.36 (dd, J=10.3, 2.1 Hz, 1H), 6.38 (d, J=1.5 Hz, 1H), 5.55 (dd, J=51.7, 2.1 Hz, 1H), 4.28 (t, J=10.8 Hz, 1H), 3.82-3.75 (m, 1H), 3.75-3.71 (m, 1H), 3.67-3.53 (m, 4H), 2.43 (d, J=1.3 Hz, 3H), 1.92 (s, 3H). $^{13}$C NMR (101 MHz, Methanol-d$_4$) δ 175.4, 169.1, 161.0, 154.7 (dd, J=248.1, 2.9 Hz), 154.3, 146.3 (dd, J=254.9, 4.7 Hz), 140.2 (dd, J=10.8, 2.8 Hz), 135.5 (dd, J=17.9, 12.6 Hz), 118.7 (d, J=9.1 Hz), 116.0, 106.7 (dd, J=23.0, 3.5 Hz), 104.3 (d, J=12.7 Hz), 90.8 (d, J=186.1 Hz), 75.9, 73.1, 69.4, 64.1, 54.4 (d, J=18.7 Hz), 46.9, 22.7, 18.7. $^{19}$F NMR (282 MHz, CDCl$_3$) δ −123.8, −139.2, −214.1. HRMS (ESI) m/z: Calcd. For C$_{21}$H$_{23}$F$_3$N$_2$O$_{10}$ ([M+H]+): 521.1383; found: 521.1377.

Synthesis of methyl 5-acetamido-7,8,9-tri-O-acetyl-3-fluoro-4-[(N',N''-di-tert-butoxy-carbonyl)guanidine]-3,4,5-trideoxy-2α-(4-methyl-6,8-difluoromethylumbelliferyl)-D-glycero-D-galactononulopyranosonate (8)

To a stirred solution of compound 7 (90 mg, 0.13 mmol) in EtOAc (5.0 mL) was added Pd/C (10%, 9.0 mg), N, N'-di-Boc-N''-trifluoromethanesulfonylguanidine[58] (64 mg, 0.17 mmol) and DIPEA (32 μL) at 25° C. The resulting solution was evacuated and filled with hydrogen three times, and the mixture was stirred under H$_2$ atmosphere for 4 h (Note: do not stirred under H$_2$ atmosphere more than 4 h because F$_2$Mu will be cleaved). The reaction mixture was filtered through a short pad of Celite and washed with EtOAc. The solvent was removed under vacuum and the residue was purified using flash column chromatography (10:10:1 EtOAc/petroleum ether/MeOH) to give 8 as a white solid (63 mg, 45%). Recorded NMR spectra (not shown). $^1$H NMR (300 MHz, Chloroform-d) δ 11.29 (s, 1H, NH), 8.90 (d, J=6.9 Hz, 1H, NH), 7.13 (dd, J=10.0, 2.2 Hz, 1H, F$_2$Mu), 6.32 (d, J=1.5 Hz, 1H, F$_2$Mu), 5.98 (d, J=8.4 Hz, 1H, NH), 5.38 (d, J=50.6 Hz, 1H, H-3), 5.18 (dd, J=7.9, 2.0 Hz, 1H, H-7), 4.81 (ddd, J=8.2, 6.5, 2.8 Hz, 1H, H-8), 4.54-4.18 (m, 2H, H-4, H-5), 4.07-4.00 (m, 1H, H-9), 3.97 (m, 1H, H-6), 3.93 (s, 3H, OMe), 3.80 (dd, J=12.3, 6.4 Hz, 1H, H-9), 2.42 (d, J=1.3 Hz, 3H, F$_2$Mu), 2.16 (s, 3H), 1.93 (s, 3H), 1.86 (s, 3H), 1.83 (s, 3H), 1.49 (s, 9H), 1.46 (s, 9H). $^{13}$C NMR (75 MHz, Chloroform-d) δ 170.8, 170.4, 170.4, 169.5, 164.8 (d, J=3.1 Hz), 162.9, 159.2, 156.9, 153.1 (dd, J=248.8, 1.8 Hz), 152.5, 151.4, 144.95 (dd, J=256.0, 4.2 Hz), 139.3 (dd, J=10.7, 2.4 Hz), 131.1 (dd, J=17.4, 12.5 Hz), 118.4 (d, J=8.4 Hz), 116.0, 105.8 (dd, J=22.5, 3.6 Hz), 99.2 (d, J=16.0 Hz, C2), 87.2 (d, J=192.8 Hz, C3), 84.2, 79.8, 74.5 (C6), 68.7 (C8), 67.4 (C7), 62.2 (C9), 53.8 (OMe), 51.5 (d, J=18.2 Hz, C4), 45.1 (d, J=3.6 Hz, C5), 28.3, 28.1, 23.1, 20.9, 20.9, 20.7, 18.9. $^{19}$F NMR (282 MHz, Chloroform-d) 6-128.02, −142.36, −214.44. HRMS: Calcd. For C$_{39}$H$_{49}$F$_3$N$_4$O$_{17}$ ([M+Na]+): 925.2943; found: 925.2921.

Synthesis of 5-acetamido-3-fluoro-4-guanidine-3,4,5-trideoxy-2α-(4-methyl-6,8-difluoromethylumbelliferyl)-D-glycero-D-galactononulopyrano-sylnoic acid (3)

To a stirred solution of compound 8 (48 mg, 53 μmmol) in dry MeOH (4.0 mL) was added a small piece of sodium at 25° C. under Ar. The reaction was stirred for 1 h. 0.5 M NaOH (1.0 mL) was added and the resulting solution was stirred at 25° C. for 2 h. The reaction was neutralized with Amberlite™ (IR-120 H$^+$), filtered and washed with MeOH. The solvent was evaporated under vacuum and the resulting residue was dissolved in 3 mL TFA. The solution was stirred for 2 h at 25° C. TFA was removed under vacuum and the residue was purified using flash column chromatography (8:2:1 EtOAc/MeOH/Water) to give 3 as a white solid (16 mg, 54%). Recorded NMR spectra (not shown). $^1$H NMR (300 MHz, Methanol-d$_4$) δ 7.4 (dd, J=10.3, 2.1 Hz, 1H, F2Mu), 6.4 (d, J=1.5 Hz, 1H, F2Mu), 5.4 (dd, J=51.9, 2.2 Hz, 1H, H-3), 4.8-4.7 (m, 1H, H-4), 4.4 (t, J=10.6 Hz, 1H, H-5), 3.7-3.5 (m, 5H, H-6, H-7, H-8, H-9), 2.4 (d, J=1.3 Hz, 3H, F2Mu), 1.6 (s, 3H). $^{13}$C NMR (75 MHz, Methanol-d$_4$) δ 173.9, 169.7 (d, J=2.7 Hz), 160.9, 158.9, 154.8 (d, J=251.5 Hz), 154.3, 146.6 (dd, J=250.5, 4.4 Hz), 140.0 (d, J=10.5 Hz), 135.2, 118.8 (d, J=9.4 Hz), 116.1, 106.8 (dd, J=22.9, 3.5 Hz), 103.9 (d, J=13.2 Hz), 91.0 (d, J=185.9 Hz), 75.3, 73.6, 68.8, 64.0, 55.1 (d, J=17.3 Hz), 47.7, 22.5, 18.7, 14.5. $^{19}$F NMR (282 MHz, Methanol-d$_4$) δ−127.4, −143.2, −216.3 HRMS (ESI): Calcd. For C$_{22}$H$_{25}$F$_3$N$_4$O$_{10}$ ([M−H]−): 561.1445; found: 561.1446.

EXAMPLES

Various alternative embodiments and examples are described herein. These embodiments and examples are illustrative and should not be construed as limiting the scope of the invention.

Example 1: General Titration Principles

Figure 5:
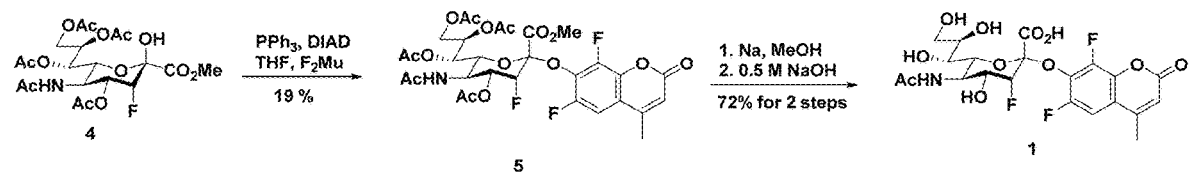
FIG. 5 shows a synthetic route to titration reagent 1.
Figure 6:
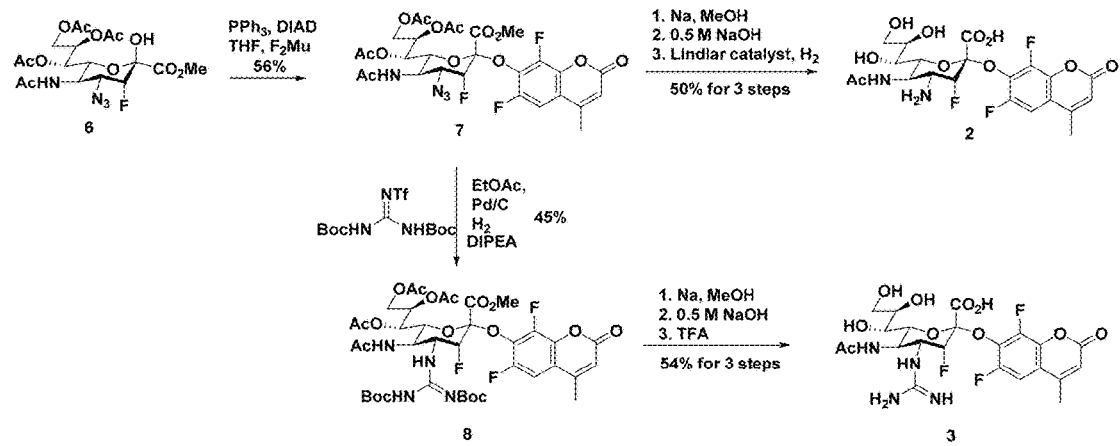
FIG. 6 shows a synthetic route to reagents 2 and 3.

The 2,3-difluorosialic acid derivatives function as substrates for which the second step ($k_{hydr}$) is very slow (FIG. 1). The fluorine at C-3 destabilizes the oxocarbenium ion-like transition states slowing both steps ($k_i$ and $k_{hydr}$) while the anomeric fluoride at C-2 is a sufficiently good leaving group that $k_i \gg k_{hydr}$. To provide specificity toward influenza NA and to further slow $k_{hydr}$, an ammonium or guanidinium group is installed at C-4. These cationic substituents occupy an anionic pocket in the active site of the viral enzyme that is not present in the human NA, thus stabilising the sialyl-enzyme intermediate.[51] This class of reagent serves as the basis for an active site titrant, as the fluorine at C-2 can be replaced by a sufficiently activated chromogenic or fluorogenic leaving group that is accommodated by the enzyme, as shown in FIG. 1. 6,8-difluorocoumarin ($F_2$Mu, pKa 4.7)[52] may act as the aglycone and fluorogenic leaving group, as it represents a good balance of size, sensitivity and reactivity. Furthermore, an axial fluorine at C-3 slows both enzymatic and non-enzymatic glycosyl transfer reactions. Therefore, compound 1 with an axial fluorine at C-3 was synthesized by a Mitsunobu reaction between partially protected 3-fluoro-N-acetylneuraminic acid and $F_2$Mu, followed by deprotection (FIG. 5). FIG. 6 shows the synthetic route to compounds 2 and 3. The general mechanism of action of titration agents 1-3 is shown in FIG. 1 and FIG. 2. Binding of the reagent to the enzyme active site leads to the first step in catalysis: cleavage of the sialoside linkage, with formation of a covalent 3-fluorosialosyl-enzyme intermediate and release of one equivalent of fluorophore or chromophore per enzyme equivalent. The second step in catalysis, hydrolysis of the 3-fluorosialosyl enzyme, is very slow, or does not even occur. The consequence is the relatively rapid release of one equivalent of fluorophore or chromophore, which can be readily quantitated. By constructing standard curves of fluorescence or UV/Vis absorbance vs concentration with authentic samples of the fluorophore or chromophore, the concentration of the fluorophore or chromophore released in the enzyme experiment can be calculated. Since the reaction product is released in a stoichiometric manner relative to the neuraminidase, the concentration of active neuraminidase can be calculated.

Example 2: Titration of Sialidases from *Micromonospora viridifaciens* (NedA)

Initial testing was performed with the sialidase from *Micromonospora viridifaciens* (NedA), monitoring reaction using a fluorimeter.[54] This enzyme belongs to the GH33 family in the CAZy classification,[55] while the viral sialidases/neuraminidases belong to family GH34. All experiments were carried out in a 50 mM Tris/20 mM CaCl$_2$ buffer, pH 7.6 with a Cary Eclipse™ fluorescence spectrophotometer. The background fluorescence $F_{background}$ of 500 nM of titration reagent 1 in 4.5-mL cuvettes was monitored for about 1 min (Ex 353 nm, Em 451 nm). The titration was started by the addition of varying concentrations of NedA (0.7 nM to 143 nM) (final volume 1.0 mL) and the fluorescence was monitored continuously for another 10 min (Ex 353 nm, Em 451 nm). The steady-state fluorescence signal was extrapolated to the zero point (the addition of the titration reagent 1) to get $F_0$. The fluorescent response $F_{response}$ was calculated with Equation 1:

$$F_{respond} = F_0 - F_{background} \qquad \text{Equation 1}$$

Figure 7:
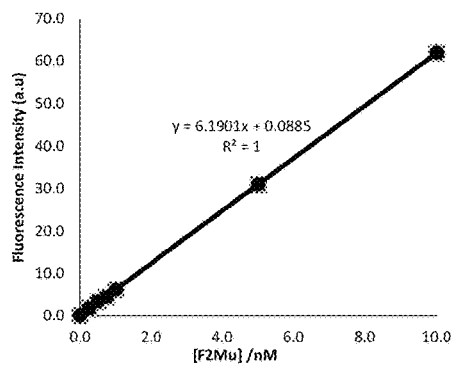
FIG. 7 shows a (A) calibration curve of F₂Mu (0.2 nM to 10 nM); and a (B) calibration curve of F₂Mu (10 nM to 100 nM).
Figure 7:
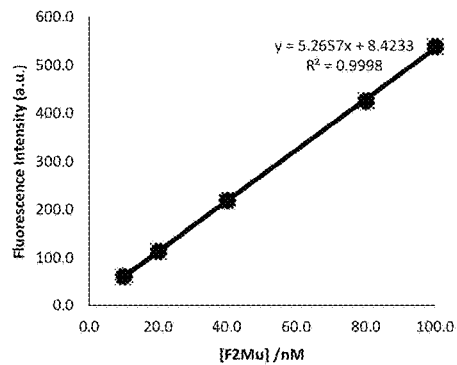

$F_2$Mu released was calculated based on the calibration curve of $F_2$Mu (FIG. 7). It should be noted that a stock solution of 1 undergoes slow spontaneous hydrolysis and that after some time, a significant amount of $F_2$Mu will be present in the solution, producing a large background fluorescent signal. However, this issue can be solved by extracting $F_2$Mu out of the solution with EtOAc before the titration reaction. As can be seen in FIG. 3A, a classical burst phase of increased fluorescence was observed, followed by a steady-state phase indicating that substrate turnover was occurring. In such cases, the active enzyme concentration can be measured from the amplitude of the burst phase after extrapolating the steady state portion back to the y-axis. If $k_i \gg k_{hydr}$ a full-size burst (converted to [$F_2$Mu] using the fluorescence response obtained with a standard curve) is obtained: if the two rate constants are closer the burst amplitude is modulated by the term $\{k_i/(k_i + k_{hydr})\}^2$.[49] As seen in FIG. 3B, a plot of the burst size vs the concentration of NedA based on $A^{280}$ is linear down to at least 0.7 nM concentrations.

Example 3: Titration of Influenza N2 Subtype NA from A/Hong Kong/1/68 (H3N2)

All experiments were carried out in a 50 mM Tris/20 mM CaCl$_2$ buffer, pH 7.6 with a Cary Eclipse™ fluorescence spectrophotometer. The viral stock solution was prepared by adding 300 µL of buffer, 50 µL 1% BSA and 50 µL 4% Triton X-100 to 100 µL of virus solution that had been treated with NP-40 to kill any viral infectivity. 100 µL of the virus solution was added to a 4.5-mL cuvette containing 890 µL of buffer. The background fluorescent signal of the virus solution was zeroed. The titration was started by the addition of 10 µL of 100 µM of the titration reagent 3 and fluorescence was monitored until completion to get $F_{final}$. In a separate cuvette the fluorescence of 1 µM of 3 was measured ($F_{background}$, the background fluorescent signal of $F_2$Mu presented in the solution). The fluorescence respond $F_{response}$ was calculated with Equation 2:

$$F_{response} = F_{final} - F_{background} \qquad \text{Equation 2}$$

Figure 4:
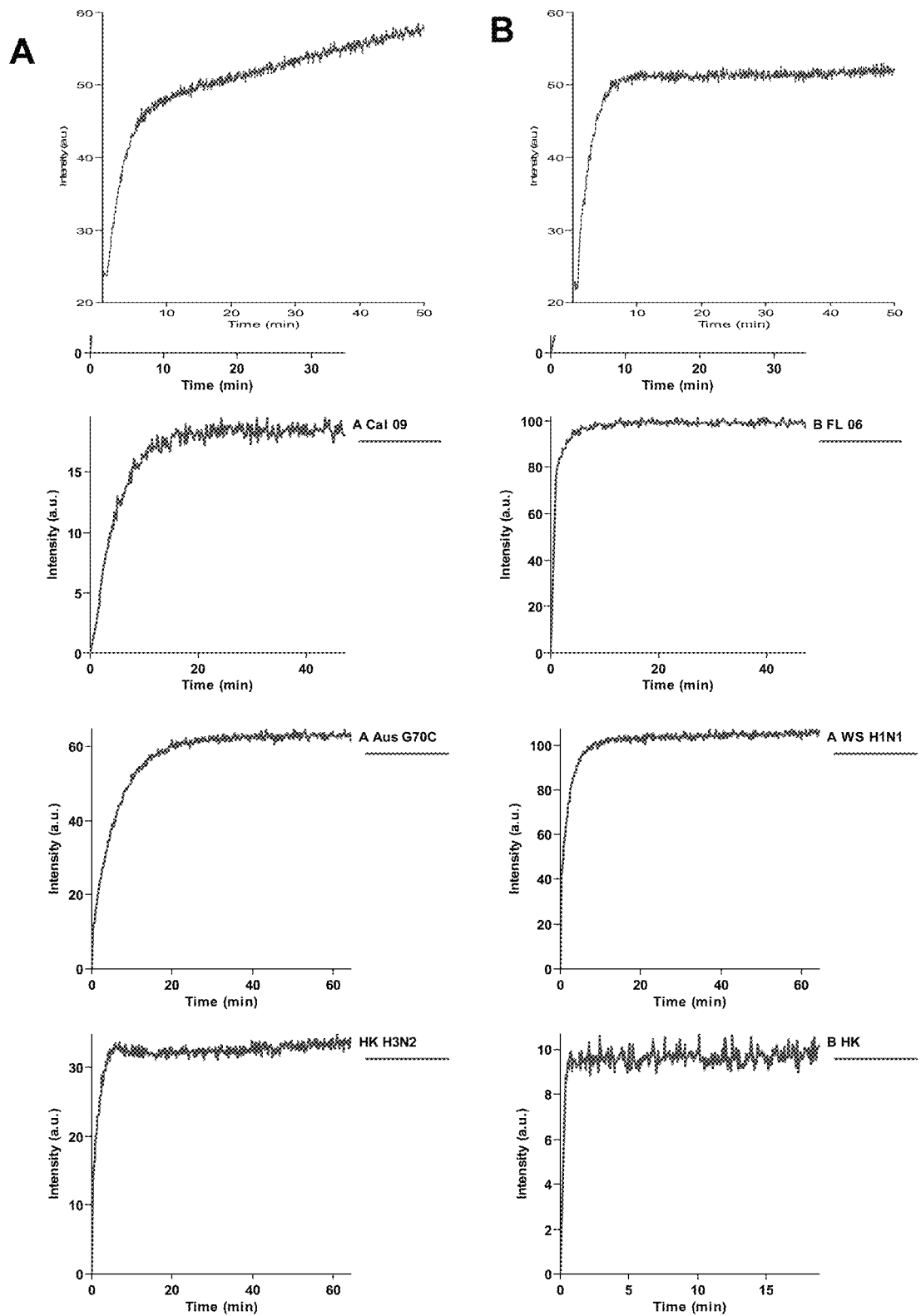
FIG. 4 shows (A) a titration of N2 with 10 µM of 2; (B) a titration of N2 with 1 µM of 3; and (C) a titration of eight strains of virus with 1 µM of 3.
Figure 8:
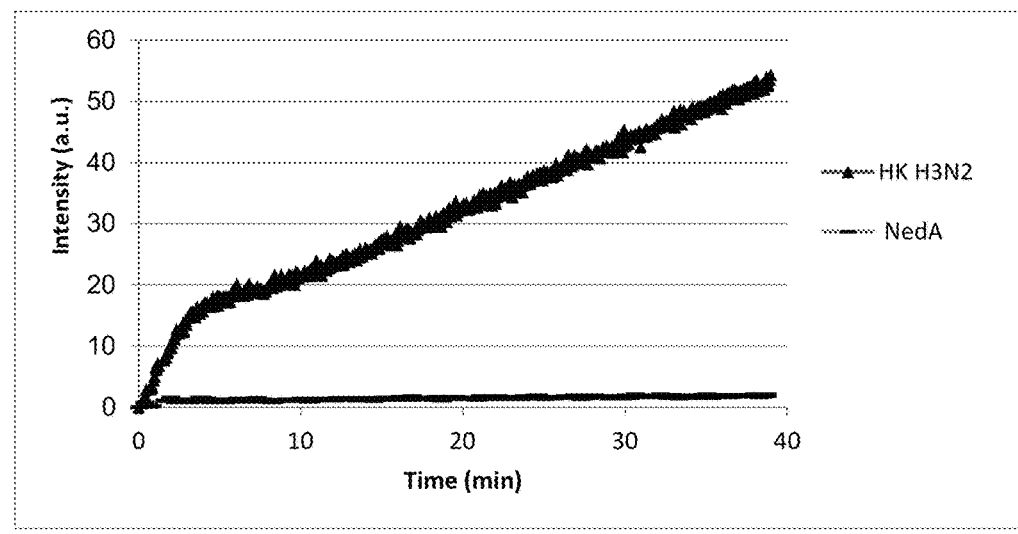
FIG. 8 shows a titration of A/Hong Kong/1/68 H3N2 with 1 µM of 1 (triangle), and titration of NedA with 1 µM of 3 (dash).

$F_2$Mu released was calculated based on the calibration curve of $F_2$Mu (FIG. 7). When 1 was used to titrate influenza N2 subtype neuraminidase from A/Hong Kong/1/68 (H3N2) (N2) a burst was indeed seen, but significant turnover was also observed at a rate much closer to that of the first step (FIG. 8). Incubation of 2 with N2 produced a burst, but significant turnover was still observed, although turnover was substantially slower than with 1. Introducing a guanidinium group at C-4 resulted in no detectable turnover at all, while a rapid initial burst was observed for 3 (FIG. 4).

Example 4: Titration of NA Subtypes with Compound 3

Titrations with the viral-specific reagent 3 (1 µM) were performed on seven other virus strains: five of influenza A and two of influenza B. A/Australian/G70C/1997 H1N9 and B/Hong Kong/1972 were treated with various concentrations of compound 3 and the fluorescence was monitored until completion. The resulting curves were fit to a pseudo-first order decay equation to obtain the rate constant of inactivation ($k_{obs}$). The resulting $k_{obs}$ values were plotted against the corresponding inactivator concentration and fit to Equation 3 to obtain the kinetic parameters $k_i$ and $K_i$.[59] For B/Hong Kong/1972, the inactivator concentrations were well below the $K_i$ value. A $k_i/K_i$ value was therefore obtained by fit to Equation 4.

$$k_{obs} = k_i[I]/(K_i+[I]) \quad \text{Equation 3}$$

$$k_{obs} = k_i[I]/K_i \quad \text{Equation 4}$$

Figure 9:
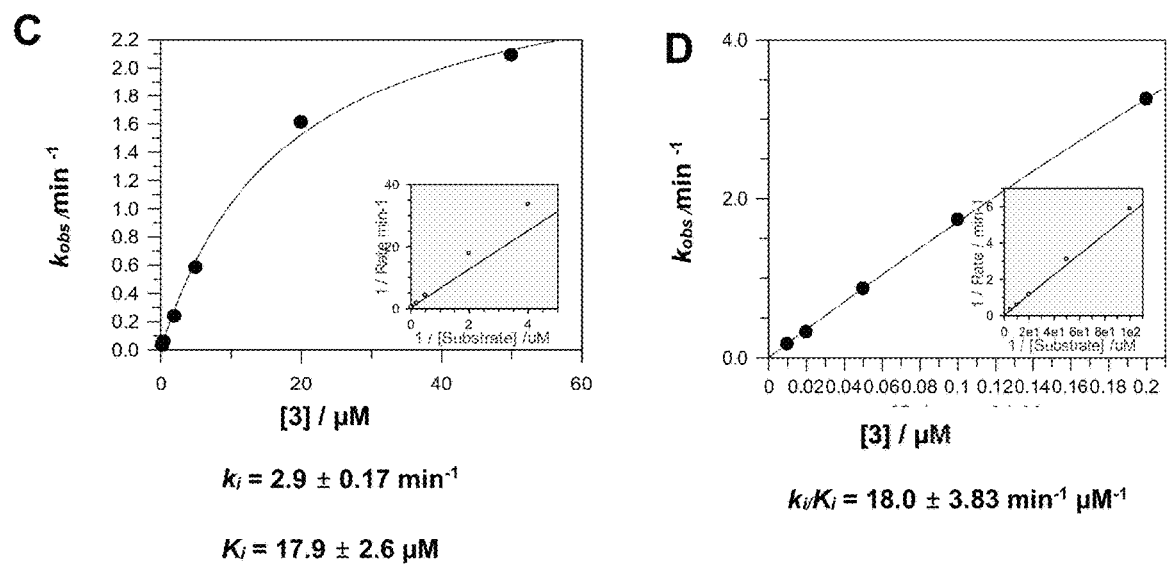
FIG. 9 shows (A) Inactivation of A/Australian/G70C/1997 with various concentrations of 3; (B) Inactivation of B/Hong Kong/1972 with various concentrations of 3; (C) Replot of $k_{obs}$ versus the concentration of 3 for A/Australian/G70C/1997; and (D) Replot of $k_{obs}$ versus the concentration of 3 for B/Hong Kong/1972.
Figure 9:
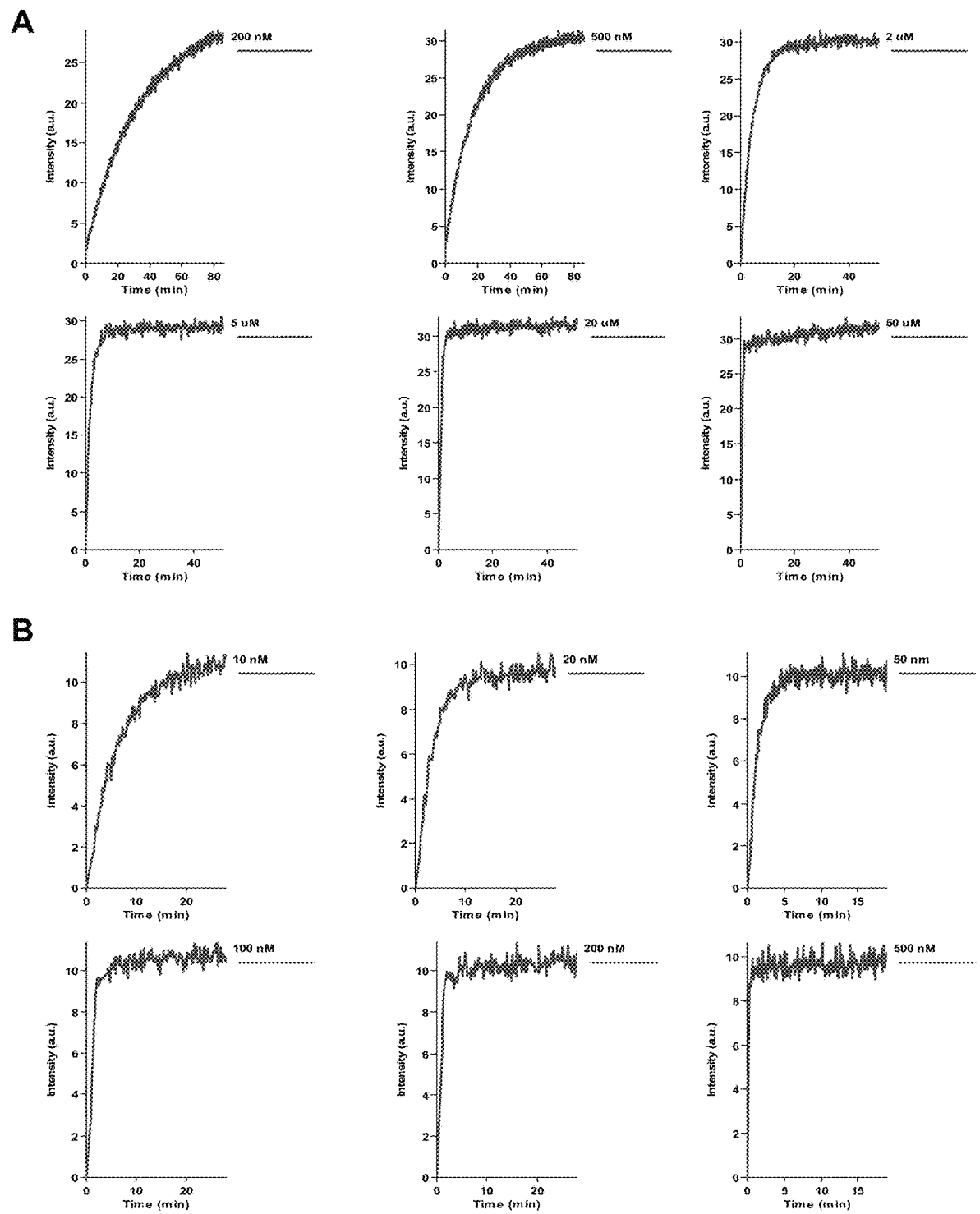
Figure 10:
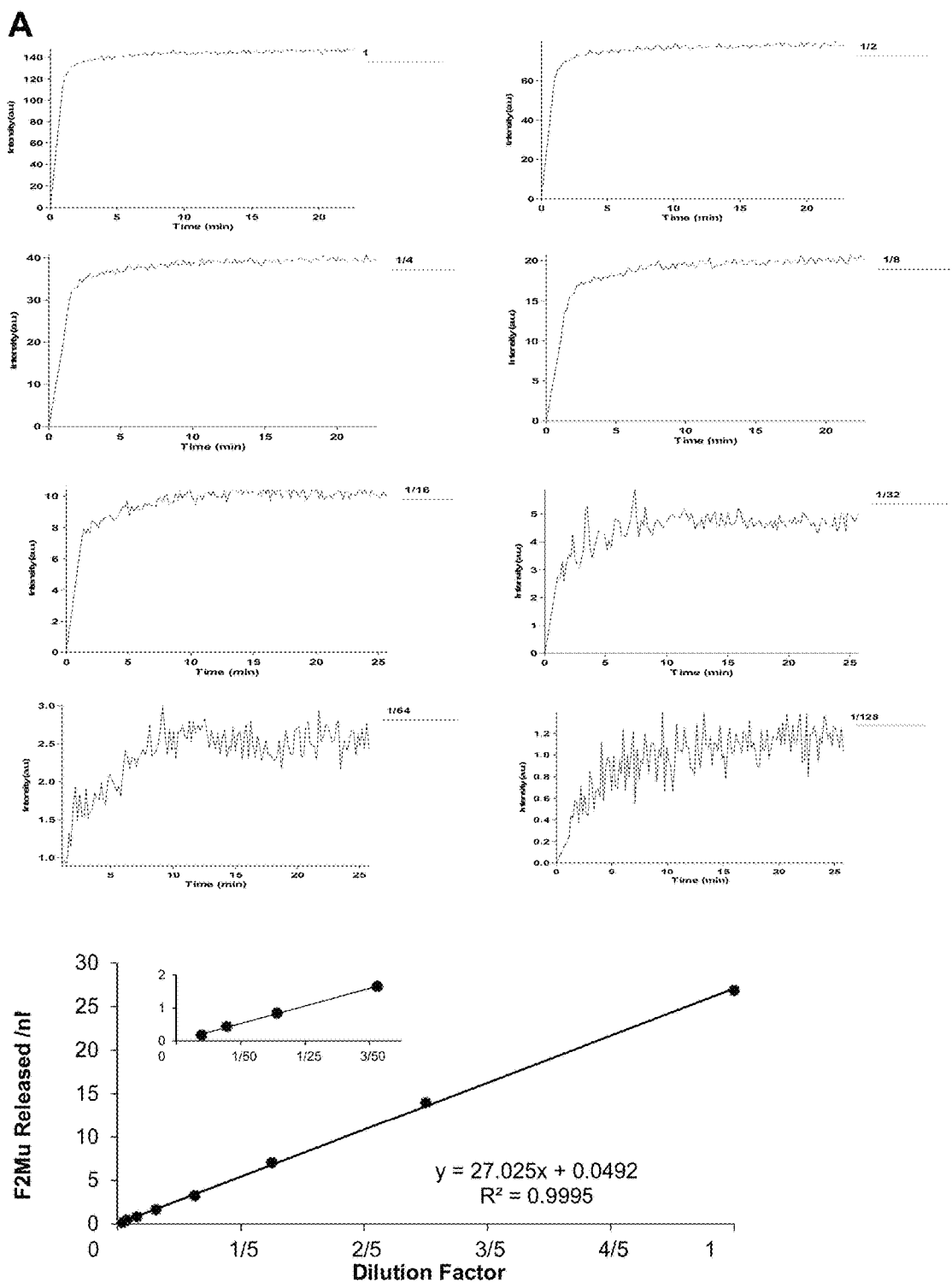
FIG. 10 shows (A) a titration of a 2-fold serial dilution of A/WS/H1N1 with 10 μM of 3; and (B) a plot of dilution factor versus the [F$_2$Mu] released: inset shows highest dilutions.
Figure 11:
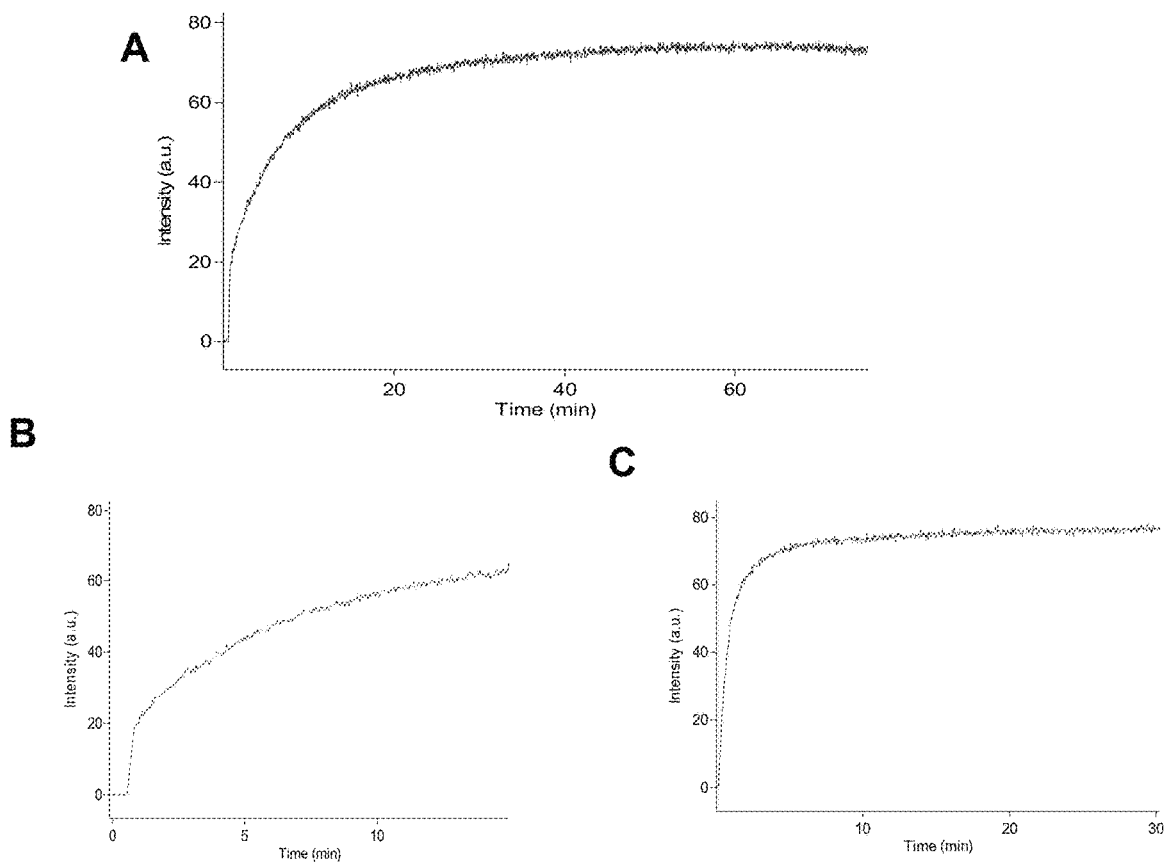
FIG. 11 shows (A) titration of Agriflu vaccine with 1.0 μM of 3; (B) Titration of Agriflu vaccine with 1 μM of 3, the first 15 min; and (C) Titration of Agriflu vaccine with 10 μM of 3.

As seen in FIG. 4C (amplitudes were normalized), titrations of all the NAs with compound 3 (1 µM) reached a plateau after about 30 min. By contrast, incubation of compound 3 with the GH33 sialidase NedA resulted in no significant response (FIG. 8). Clearly, compound 3 is an influenza-specific reagent that can be used to titrate a broad spectrum of influenza virus NAs without interference from GH33 sialidases such as the human enzymes. Influenza B NAs were inactivated much faster than those of type A: influenza B NAs were inactivated within several seconds, while those of type A took between 10 and 30 min at the concentration of 3 employed. These differences, were quantitated by measuring full kinetic parameters for two representatives: A/Australia/G70C/1997 (H1N9) and B/HK/05/1972. Titration curves for each virus were measured at a range of concentrations of compound 3 (FIG. 9) and pseudo first-order rate constants ($k_{obs}$) for inactivation at each concentration were determined by fitting to a first order expression. Fitting of these data to the expression $$k_{obs} = \frac{k_i[I]}{K_i + [I]}$$

yielded values of $k_i$=2.9 $min^{-1}$, $K_i$=17.9 µM and $k_i/K_i$=0.16 $min^{-1}$ $µM^{-1}$ for the A type N9 virus. Inactivation of the type B was significantly faster, such that only a second-order rate constant could be determined, since reaction at higher (saturating) concentrations was too fast for measurement. The rate constant obtained, $k_i/K_i$=18.0 $min^{-1}$ $µM^{-1}$, is about 110-fold greater than that for N9. Some insights can be obtained by comparison with kinetic parameters for the inactivation of N9 with the corresponding FaxGuDFSA with a fluoride leaving group ($k_i$=0.1 $min^{-1}$, $K_i$=0.41 µM).[50] The 41-fold higher $K_i$ for compound 3 suggests that the aromatic group is not as well accommodated in the active site, possibly leading to some ground state strain that is relieved at the transition state, as is implied by the 28-fold higher $k_i$ value for compound 3, despite the similar leaving group abilities (as measured by pKa values for $F_2$MU and $F^-$ of 4.7 and 3.2)[52][56]. The higher value of $k_i/K_i$ for the B virus implies that this release of steric strain is greater in the B virus.

Example 5: Sensitivity and Linearity of Response

The sensitivity and linearity of response of the reagent with virus samples were tested with a sample of the A/WS/33 (H1N1) influenza virus strain. After an initial 40-fold dilution the sample was titrated with compound 3 (10 μM, FIG. 10) and a burst corresponding to 27 nM of $F_2$Mu obtained: this equates to an initial concentration of 1.08 μM of NA in the original virus sample. Serial dilution and titration of the 27 nM sample continued to give reliable data down to a 128-fold dilution, equivalent to approximately 200 pM NA as shown in FIG. 4D.

Example 6: Determination of $k_{cat}$ and $K_m$ of Influenza NAs for Hydrolysis of 3

All experiments were carried out in a 20 mM Tris/50 mM $CaCl_2$ buffer, pH 7.6 with a Cary 4000 UV/visible Spectrophotometer™ connected to a circulating water bath at 30° C. The data were analyzed using the program GraFit 7.0™ (Erithacus™ Software). The viral stock solution was prepared by adding 300 μL of buffer, 50 μL 1% BSA and 50 μL 4% Triton X-100 to 100 μL of virus solution that had been treated with NP-40 to kill any viral infectivity. Varying concentration of Neu5AcCF3Mu were pre-incubated in the buffer at 30° C. The reaction was initiated by the addition of virus with known concentration of NA. The release of $CF_3$Mu was monitored by absorbance at 385 nm. The $k_{cat}$ and $K_m$ value were obtained by fitting the initial rates to the Michaelis-Menten equation. The true kinetic parameters for cleavage of the fluorogenic substrate 4-trifluoromethylumbelliferyl α-D-N-acetylneuraminide by the eight strains of virus are listed in TABLE 1.

TABLE 1

Kinetic parameters for hydrolysis of 3 by eight strains of virus.

| Virus | $k_{cat}$ ($sec^{-1}$) | $K_m$ (μM) | $k_{cat}/K_m$ ($\mu M^{-1}$ $sec^{-1}$) |
|---|---|---|---|
| A/Brisbane/59/2007 H1N1 | 32.6 | 41.1 | 0.79 |
| A/Brisbane/59/2007 H1N1 Oseltamivir-Resistant | 35.7 | 41.6 | 0.86 |
| A/Australia/1997 G70C H1N9 | 155.6 | 218 | 0.71 |
| A/California/07/2009 H1N1 | 76.4 | 31.9 | 2.40 |
| A/Washington/10/2008 H1N1 | 63.3 | 62.2 | 1.02 |
| A/Hong Kong/1/68 H3N2 | 76.7 | 45.6 | 1.68 |
| B/Florida/04/2006 | 26.7 | 28.6 | 0.93 |
| B/Hong Kong/05/1972 | 30.0 | 29.6 | 1.01 |

The A/Brisbane/59/2007 (H1N1) wild type and its oseltamivir-resistant mutant have similar kinetic parameters ($K_m$ 41.1 vs 41.6 uM and $k_{cat}$ 32.6 vs 35.7 sec-$^{-1}$), consistent with the previous report that H275Y mutation does not significantly alter the NA activity[57]. A/Australia/1997 G70C (H1N9) has the highest $K_m$ and $k_{cat}$ values, 218 M and 155.6 $sec^{-1}$ respectively. However, the overall catalytic efficacy $k_{cat}/K_m$ (0.71 $\mu M^{-1}$ $sec^{-1}$) is in the same range for all (0.71 to 2.4 $\mu M^{-1}$ $sec^{-1}$), providing evidence that the catalytic efficacy of NA may need to be balanced with HA activity for efficient virus propagation. Interestingly the $K_m$ and $k_{cat}$ values for influenza A and B are similar while, as seen earlier, the inactivation rate constants for influenza B NA were about 100-fold higher than those for influenza A. This differential slowing of influenza A NA is presumably either due to differential accommodation of the charged C4 substituent or greater charge development at the influenza A NA transition state, which would be destabilized more by the fluorine.

Example 7: Titration of Agriflu Vaccine with 3 at Various Concentrations

Agriflu contains two influenza A strains, A/California/07/2009 (H1N1) and A/Switzerland/9715293/2013 (H3N2), and one influenza B strain, B/Brisbane/9/2014. Indeed, when titrated with compound 3 at a low (1 μM) concentration a multi-phase reaction was observed with initial rapid reaction of the influenza B, corresponding to about 33% of the total fluorescence followed by a slower second phase corresponding to inactivation of two influenza A strains (FIGS. 11A and 11B). Increasing the concentration of compound 3 to 10 μM significantly sped up reaction, (FIG. 11C), revealing a total NA concentration of 253 nM (equivalent to 12.6 μg/mL) in the vaccine which is consistent with previous reports.[47,48]

Figure 12:
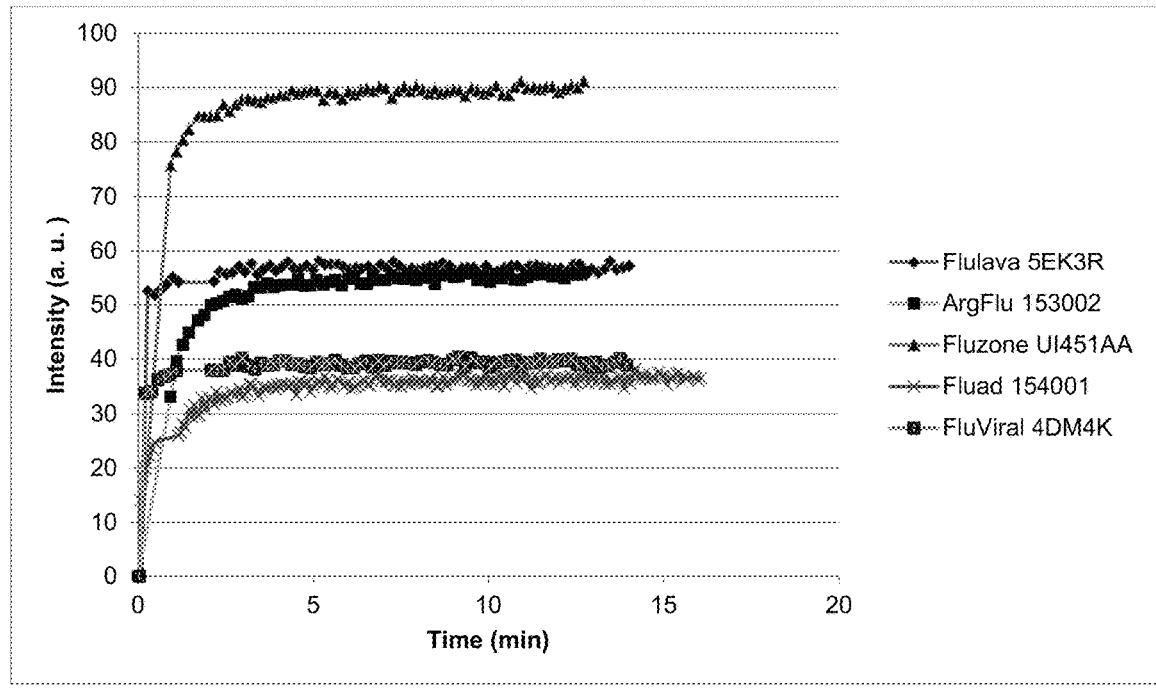
FIG. 12 shows a representative titration curves of 2015-2016 Vaccine with 10 μM of 3 (with a fluorimeter, Ex 353 nm, Em 451 nm).

Example 8: Determination of NA Concentration of 2015-2016 and 2016-2017 Flu Vaccines with FaxGuSAF2Mu Commercial flu vaccines for the 2015-2016 season from various manufacturers were purchased in a pharmacy and analyzed for their NA concentration. The results are summarized in TABLE 2. The respective titration curves of the 2015-2016 vaccines with 10 µM of FaxGuSAF2Mu on a fluorimeter with an excitation wavelength of 353 nm and an emission wavelength of 451 nm are shown in FIG. 12.

TABLE 2

Determination of NA Concentration of 2015-2016 Vaccine with FaxGuSAF2Mu

| 2015-2016 Vaccine | Lot Number | NA Concentration (nM) | NA Concentration (nM)/strain |
|---|---|---|---|
| Fluzone (Quad) | UI494AA | 312.1 | 78 |
| Fluzone (Quad) | UI451AA | 330.8 | 82.5 |
| AgriFlu | 153001 | 203.4 | 67.8 |
| FluAd | 154001 | 66.1 | 22 |
| FluAd | 154002 | 54.9 | 18.3 |
| Fluviral | 4DM4K | 143.5 | 47.8 |
| Flulava (Quad) | 5EK3R | 214.7 | 53.6 |

Accordingly, the NA concentration in flu vaccines for the 2016-2017 season were determined and the results summarized in TABLE 3.

TABLE 3

Determination of NA Concentration of 2016-2017 Vaccine with FaxGuSAF2Mu.

| 2016-2017 Vaccine | Lot Number | NA Concentration (nM) | NA Concentration (nM)/strain |
|---|---|---|---|
| AgriFlu | 165001 | 168.6 | 56.2 |
| AgriFlu | 164701 | 137.9 | 46.0 |
| Fluviral | F5B7A | 94.1 | 31.4 |
| Fluzone (Quad) | UI640AA | 282.1 | 70.5 |
| Fluzone HD (Quad) | UI685AA | 568.6 | 142.2 |
| FluLaval(Quad) | 24B37 | 220.3 | 55.1 |
| Fluad | 166701 | 76.1 | 25.4 |
| Flumist | HL2478 | 33.3 | 11.1 |

Example 9: Effect of Reagents

In order to render the virus non-infective, either for biochemical studies or for use as a vaccine, the virus must be treated with reagents that destroy its ability to replicate, but otherwise hopefully minimally affect the integrity of its components. Reagents such as detergents or covalent modifiers are frequently employed for this purpose. However, assessment of the effects of these reagents on the integrity of the NA are difficult to assess. The titration compounds described herein allow for the NA concentration to be determined directly.

Figure 13:
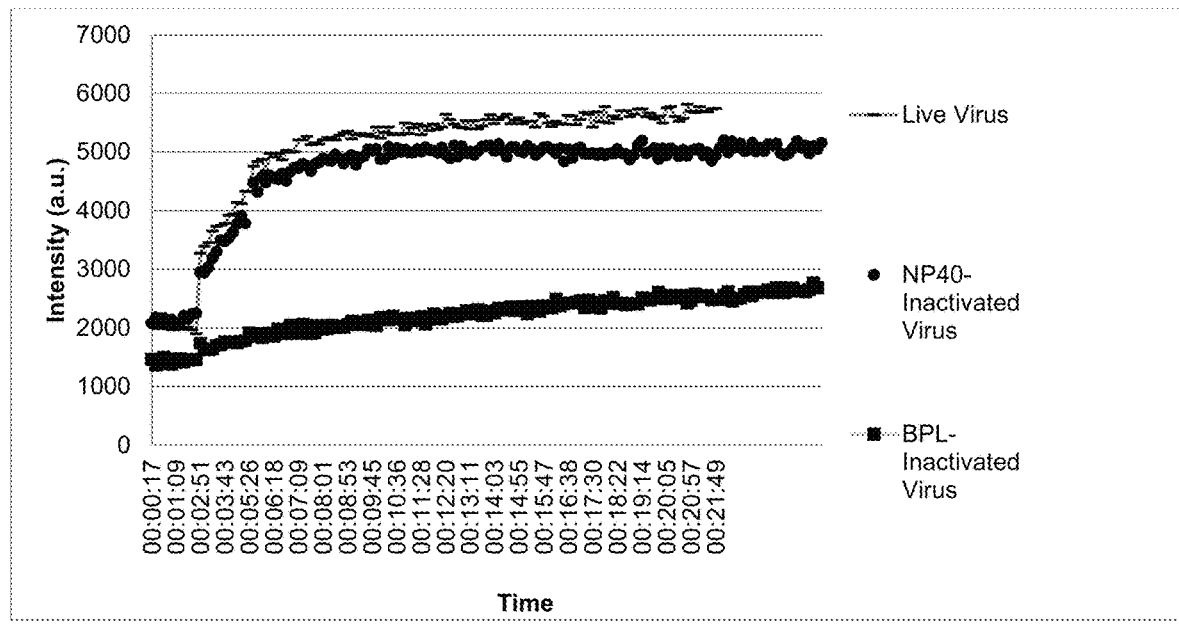
FIG. 13 shows a titration curve of live virus, NP40 detergent-inactivated virus and β-propiolactone-inactivated virus with 10 μM of 2 (with a plate reader), but NP40 detergent did not affect the NA activities, while β-propiolactone dramatically reduced NA activities.

Treatment of virus with surfactants, such as e.g. sodium dodecyl sulfate or NP40 results in almost complete removal of viral lipid and thereby leads to inactivation of the virus. Therefore, the effect that these different detergents and reagents might have on the NA-analytical test was investigated. The effect of these different reagents was assessed by titrating virus inactivated by (a) NP40 detergent and (b) β-propiolactone with 10 µM of FaxAmSAF2Mu as shown in FIG. 13. Compared to live virus, NP40 detergent did not affect the NA activity, while β-propiolactone significantly reduced NA activities, suggesting that some covalent modification has likely occurred.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings. Titles, headings, or the like are provided to enhance the reader's comprehension of this document, and should not be read as limiting the scope of the present invention.

REFERENCES

[1] H.-L. Yen, *Curr. Opin. Virol.* 2016, 18, 126-134.
[2] F. S. Dawood, A. D. Iuliano, C. Reed, M. I. Meltzer, D. K. Shay, P.-Y. Cheng, D. Bandaranayake, R. F. Breiman, W. A. Brooks, P. Buchy, et al., *Lancet Infect. Dis.* 2012, 12, 687-695.
[3] M. Lakadamyali, M. J. Rust, X. Zhuang, *Microbes Infect.* 2004, 6, 929-36.
[4] J.-S. Casalegno, O. Ferraris, V. Escuret, M. Bouscambert, C. Bergeron, L. Linés, T. Excoffier, M. Valette, E. Frobert, S. Pillet, et al., *PLoS One* 2014, 9, e104009.
[5] R. Wagner, M. Matrosovich, H.-D. Klenk, *Rev. Med. Virol.* 2002, 12, 159-66.
[6] D. J. Benton, S. R. Martin, S. A. Wharton, J. W. McCauley, *J. Biol. Chem.* 2015, 290, 6516-6521.
[7] M. J. Memoli, P. A. Shaw, A. Han, L. Czajkowski, S. Reed, R. Athota, T. Bristol, S. Fargis, K. Risos, J. H. Powers, et al., *MBio* 2016, 7, e00417-16.
[8] M. L. Clements, R. F. Betts, E. L. Tierney, B. R. Murphy, *J. Clin. Microbiol.* 1986, 24, 157-160.
[9] J. L. Virelizier, A. C. Allison, G. C. Schild, *Br. Med. Bull.* 1979, 35, 65-68.
[10] R. B. Couch, R. L. Atmar, L. M. Franco, J. M. Quarles, J. Wells, N. Arden, D. Ni??o, J. W. Belmont, *J. Infect. Dis.* 2013, 207, 974-981.
[11] A. S. Monto, J. G. Petrie, R. T. Cross, E. Johnson, M. Liu, W. Zhong, M. Levine, J. M. Katz, S. E. Ohmit, *J. Infect. Dis.* 2015, 212, 1191-1199.
[12] A. Monto, A. Kendal, *Lancet* 1973, 301, 623-625.
[13] G. C. Schild, R. W. Newman, *J Hyg.* (Lond). 1969, 67, 353-365.
[14] B. R. Murphy, J. A. Kasel, R. M. Chanock, *N. Engl. J. Med.* 1972, 286, 1329-1332.
[15] T. J. Wohlbold, F. Krammer, *Viruses* 2014, 6, 2465-2494.
[16] A. Jagadesh, A. A. A. Salam, P. P. Mudgal, G. Arunkumar, *Arch. Virol.* 2016, 161, 2087-2094.

[17] R. A. Bright, K. M. Neuzil, Y. Pervikov, L. Palkonyay, *Vaccine* 2009, 27, 6366-6369.

[18] J. M. Wood, G. C. Schild, R. W. Newman, V. Seagroatt, *J. Biol. Stand.* 1977, 5, 237-247.

[19] A. S. Gambaryan, M. N. Matrosovich, *J. Virol. Methods* 1992, 39, 111-123.

[20] O. Blixt, S. Head, T. Mondala, C. Scanlan, M. E. Huflejt, R. Alvarez, M. C. Bryan, F. Fazio, D. Calarese, J. Stevens, et al., *Proc. Natl. Acad. Sci. U.S.A* 2004, 101, 17033-17038.

[21] J. Stevens, O. Blixt, L. Glaser, J. K. Taubenberger, P. Palese, J. C. Paulson, I. A. Wilson, *J. Mol. Biol.* 2006, 355, 1143-1155.

[22] a a Ghate, G. M. Air, *Eur. J. Biochem.* 1998, 258, 320-31.

[23] X. Zhu, R. McBride, C. M. Nycholat, W. Yu, J. C. Paulson, I. a. Wilson, *J Virol.* 2012, 86, 13371-13383.

[24] M. Prevato, I. Ferlenghi, A. Bonci, Y. Uematsu, G. Anselmi, F. Giusti, S. Bertholet, F. Legay, J. L. Telford, E. C. Settembre, et al., *PLoS One* 2015, 10, 1-18.

[25] R. Xu, X. Zhu, R. McBride, C. M. Nycholat, W. Yu, J. C. Paulson, I. A. Wilson, *J Virol.* 2012, 86, 9221-32.

[26] P. M. Schmidt, R. M. Attwood, P. G. Mohr, S. A. Barrett, J. L. McKimm-Breschkin, *PLoS One* 2011, 6, e16284.

[27] H.-L. Yen, C.-H. Liang, C.-Y. Wu, H. L. Forrest, A. Ferguson, K.-T. Choy, J. Jones, D. D.-Y. Wong, P. P.-H. Cheung, C.-H. Hsu, et al., *Proc. Natl. Acad. Sci. U.S.A* 2011, 108, 14264-14269.

[28] P. J. Campbell, S. Danzy, C. S. Kyriakis, M. J. Deymier, A. C. Lowen, J. Steel, *J Virol.* 2014, 88, 3802-14.

[29] W. Choi, J. Y. Shin, H. E. Jeong, M. J. Jeong, S. J. Kim, J. Y. Lee, C. Kang, *Osong Public Heal. Res. Perspect.* 2013, 4, 323-328.

[30] H. Yen, N. A. Ilyushina, R. Salomon, R. G. Webster, E. A. Govorkova, E. Hoffmann, *J. Virol.* 2007, 04, 12418-12426.

[31] J. A. L. Ives, J. A. Carr, D. B. Mendel, C. Y. Tai, R. Lambkin, L. Kelly, J. S. Oxford, F. G. Hayden, N. A. Roberts, *Antiviral Res.* 2002, 55, 307-317.

[32] P. Simon, B. P. Holder, X. Bouhy, Y. Abed, C. A. A. Beauchemin, G. Boivin, *J. Clin. Microbiol.* 2011, 49, 715-717.

[33] Y. Abed, A. Pizzorno, X. Bouhy, G. Boivin, *Antiviral Res.* 2015, 114, 57-61.

[34] M. Z. Wang, C. Y. Tai, D. B. Mendel, *Antimicrob. Agents Chemother.* 2002, 46, 3809-3816.

[35] D. Blumenkrantz, K. L. Roberts, H. Shelton, S. Lycett, W. S. Barclay, *J. Virol.* 2013, 87, 10539-51.

[36] N. A. Ilyushina, N. V Bovin, R. G. Webster, *J. Virol.* 2012, 86, 4724-33.

[37] A. G. L'Huillier, Y. Abed, T. J. Petty, S. Cordey, Y. Thomas, X. Bouhy, M. Schibler, A. Simon, Y. Chalandon, C. Van Delden, et al., *J. Infect. Dis.* 2015, 212, 1726-1734.

[38] M. A. Rameix-Welti, F. Agou, P. Buchy, S. Mardy, J. T. Aubin, M. Veron, S. Van Der Werf, N. Naffakh, *Antimicrob. Agents Chemother.* 2006, 50, 3809-3815.

[39] K. A. Hooper, J. D. Bloom, *J. Virol.* 2013, 87, 12531-12540.

[40] D. D. Y. Wong, K.-T. Choy, R. W. Y. Chan, S. F. Sia, H.-P. Chiu, P. P. H. Cheung, M. C. W. Chan, J. S. M. Peiris, H.-L. Yen, *J Virol.* 2012, 86, 10558-70.

[41] J. Seladi-Schulman, P. J. Campbell, S. Suppiah, J. Steel, A. C. Lowen, *PLoS One* 2014, 9, 1-10.

[42] N. M. Bouvier, S. Rahmat, N. Pica, *J Virol.* 2012, 86, 7268-79.

[43] A. Pizzorno, Y. Abed, C. Rheaume, X. Bouhy, G. Boivin, *Antimicrob. Agents Chemother.* 2013, 57, 1784-1789.

[44] H.-L. Yen, J. L. McKimm-Breschkin, K.-T. Choy, D. D. Y. Wong, P. P. H. Cheung, J. Zhou, I. H. Ng, H. Zhu, R. J. Webby, Y. Guan, et al., *MBio* 2013, 4, e00396-13-e00396-13.

[45] M. Aymard, *Vaccine* 2002, 20, 59-60.

[46] T. L. Williams, J. L. Pirkle, J. R. Barr, *Vaccine* 2012, 30, 2475-2482.

[47] M. Getie-Kebtie, I. Sultana, M. Eichelberger, M. Alterman, *Influenza Other Respi. Viruses* 2013, 7, 521-530.

[48] C. Gravel, C. Li, J. Wang, A. M. Hashem, B. Jaentschke, K. Xu, B. Lorbetskie, G. Gingras, Y. Aubin, G. Van Domselaar, et al., *Vaccine* 2010, 28, 5774-5784.

[49] M. L. Bender, M. L. Begué-Cantón, R. L. Blakeley, L. J. Brubacher, J. Feder, C. R. Gunter, F. J. Kézdy, J. V Killheffer, T. H. Marshall, C. G. Miller, et al., *J. Am. Chem. Soc.* 1966, 88, 5890-913.

[50] J.-H. Kim, R. Resende, T. Wennekes, H.-M. Chen, N. Bance, S. Buchini, a. G. Watts, P. Pilling, V. a. Streltsov, M. Petric, et al., *Science* 2013, 71, 71-75.

[51] M. von Itzstein, W.-Y. Y. Wu, G. B. Kok, M. S. Pegg, J. C. Dyason, B. Jin, T. Van Phan, M. L. Smythe, H. F. White, S. W. Oliver, et al., *Nature* 1993, 363, 418-423.

[52] W. C. Sun, K. R. Gee, R. P. Haugland, *Bioorg. Med. Chem. Lett.* 1998, 8, 3107-10.

[53] S. Buchini, F. X. Gallat, I. R. Greig, J. H. Kim, S. Wakatsuki, L. M. G. Chavas, S. G. Withers, *Angew. Chemie Int. Ed.* 2014, 53, 3382-3386.

[54] K. Khazaei, J. H. F. Yeung, M. M. Moore, A. J. Bennet, *Can. J. Chem.* 2015, 93, 1207-1213.

[55] V. Lombard, H. Golaconda Ramulu, E. Drula, P. M. Coutinho, B. Henrissat, *Nucleic Acids Res.* 2014, 42, 490-495.

[56] S. Weck, K. Robinson, M. R. Smith, S. G. Withers, *Chem. Commun.* 2015, 51, 2933-2935.

[57] Y. Abed, A. Pizzorno, X. Bouhy, G. Boivin, *PLoS Pathog.* 2011, 7, 1-9.

[58] K. Feichtinger, C. Zapf, H. L. Sings, M. Goodman, *J. Org. Chem.* 1998, 3263, 3804.

[59] R. Kitz, I. B. Wilson, *J Biol. Chem.* 1962, 237, 3245.

What is claimed is:

1. A method of detecting a neuraminidase activity in a sample, the method comprising:
 (a) contacting a sample suspected of having the neuraminidase activity with a compound having the structure of Formula A or a salt thereof,

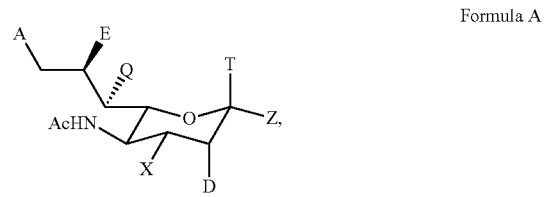

Formula A wherein,

T is selected from COOH, COO⁻ and COOR$^1$;

R$^1$ is a $C_{1-20}$ linear, branched or cyclic, saturated or unsaturated, unsubstituted alkyl group;

D is selected from F and Cl;

X is selected from $N_3$, OAc, $NH_2$, —NHC(NH)NH$_2$ and —NHC(NBoc)NHBoc;

Q is selected from H, OH and —O—(CH$_2$)n—R$^2$;

$R^2$ is a $C_{1-20}$ linear, branched or cyclic, saturated or unsaturated, unsubstituted alkyl group;

n is 2, 3, 4 or 5;

E is selected from H, OH, —O—$(CH_2)$n—$R^2$ and OAc;

A is selected from H, OH, —O—$(CH_2)$n—$R^2$ and OAc; and

Z is a chromogenic or fluorogenic group that exhibits a distinct colour and/or fluorescence when cleaved from the substrate or salts of said substrate; and (b) detecting a reaction product, wherein exposure of the neuraminidase activity to the compound results in a stoichiometric release of a detectable reaction product Z, whereby the ratio of neuraminidase to reaction product Z is 1:1 and the reaction product Z is a chromogenic or fluorogenic group that exhibits a distinct colour and/or fluorescence when cleaved from the substrate or salts of said substrate.

2. The method of claim 1, wherein the detectable reaction product exhibits a fluorescence.

3. The method of claim 1, wherein the detectable reaction product is quantified.

4. The method of claim 1, wherein the detectable reaction product is quantified to determine the amount and/or activity of neuraminidase in the sample.

5. The method of claim 1, wherein the detectable reaction product is quantified with the aid of a calibration curve or a standardized sample or standardized samples.

6. The method of claim 1, wherein the neuraminidase activity is human influenza neuraminidase activity.

7. The method of claim 1, wherein the neuraminidase activity is human influenza A neuraminidase activity and/or human influenza B neuraminidase activity.

8. The method of claim 1, wherein the sample is a crude sample; a biological; or a clinical sample.

9. The method of claim 1, wherein the sample comprises viral particles; or a vaccine.

10. The method of claim 1, wherein Z is selected from:

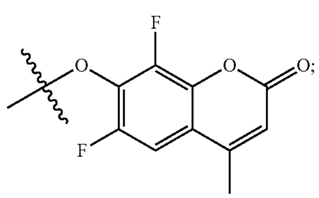

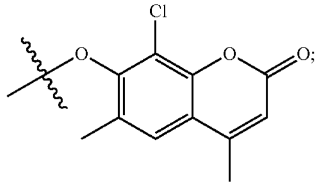

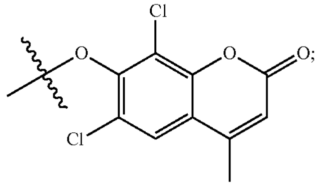

-continued

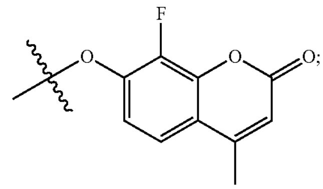

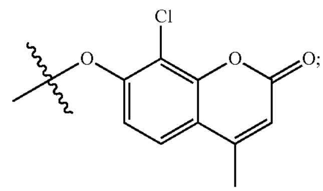

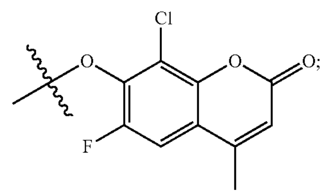

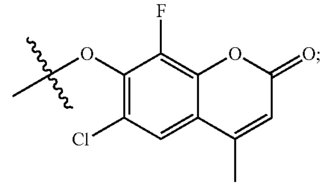

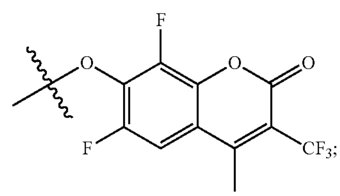

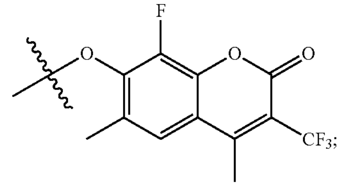

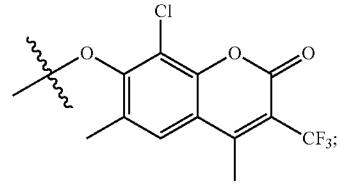

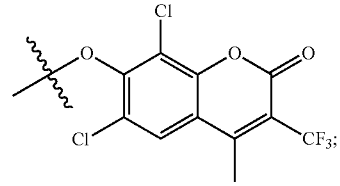

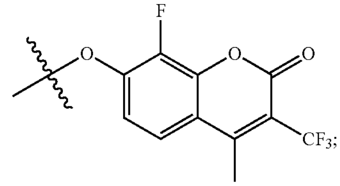

-continued
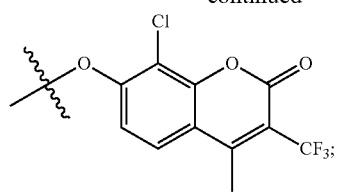
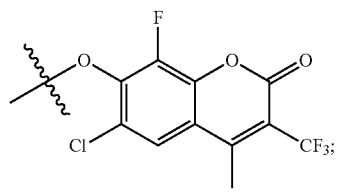
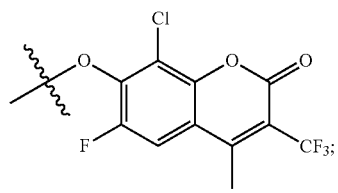
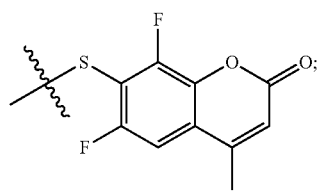
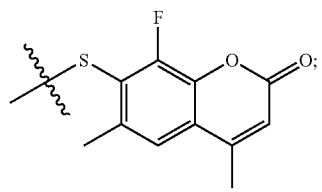
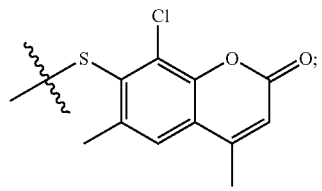
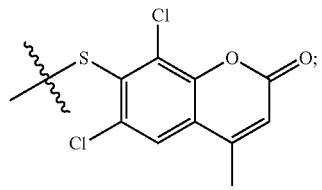
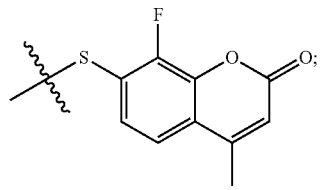
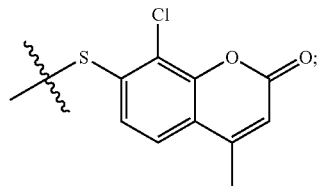
-continued
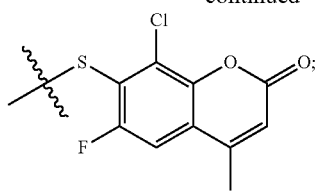
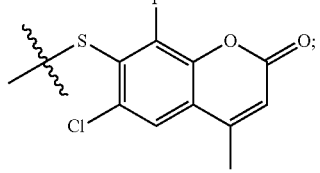
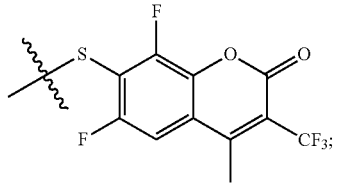
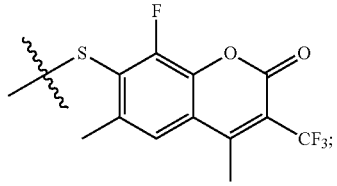
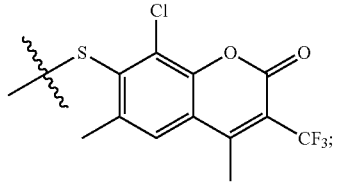
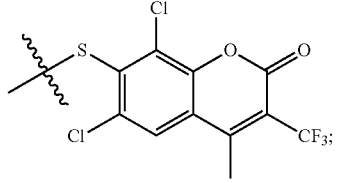
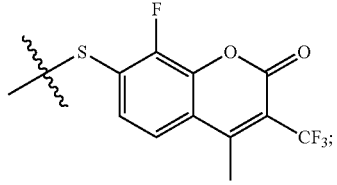
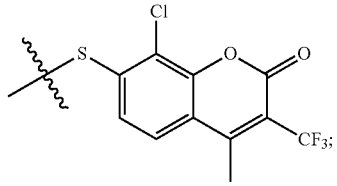
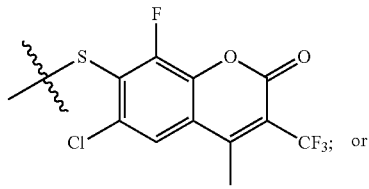 or -continued
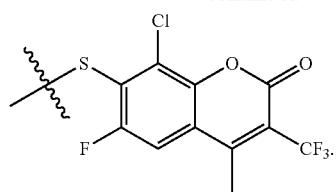
11. The method of claim 2, wherein Z is selected from:
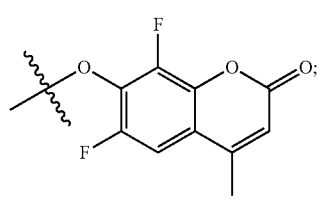
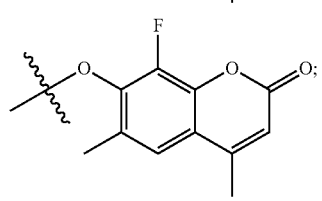
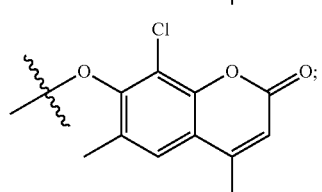
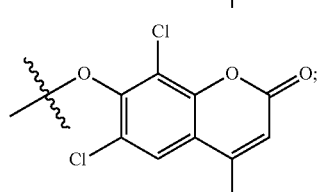
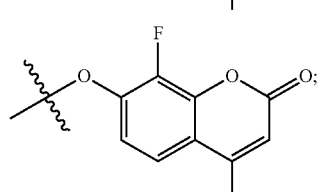
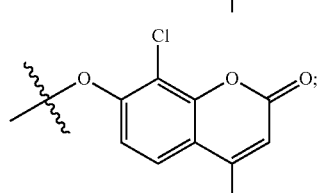
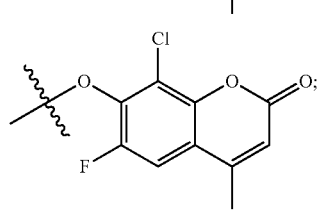
-continued
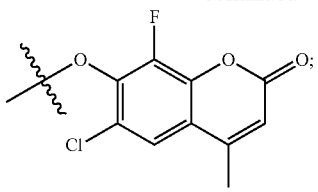
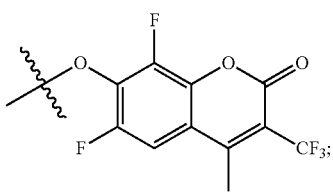
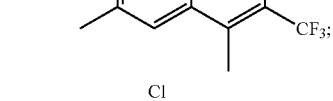
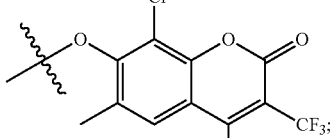
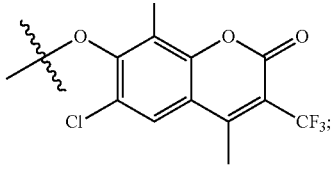
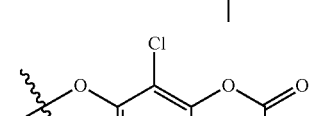
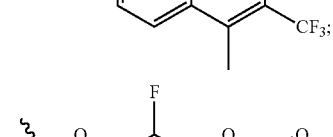
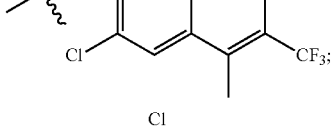
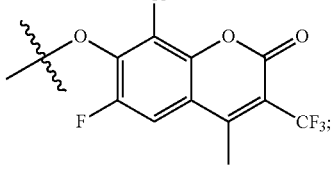

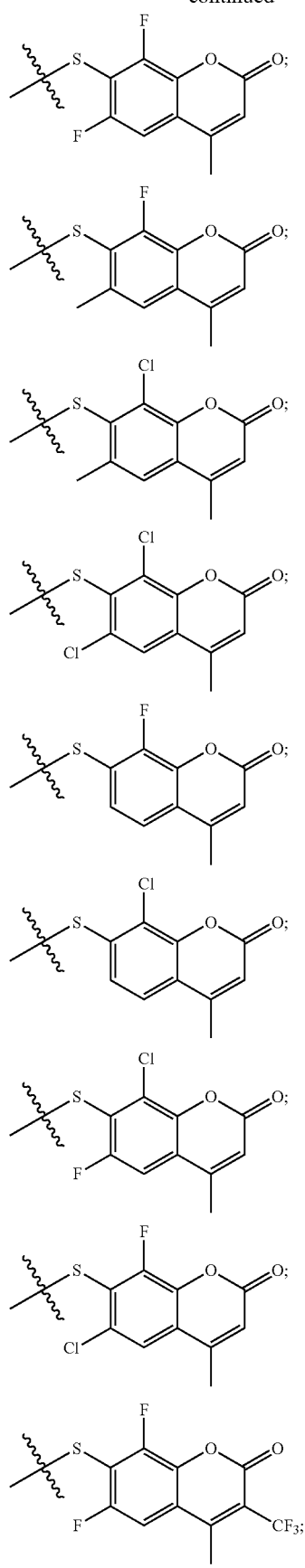
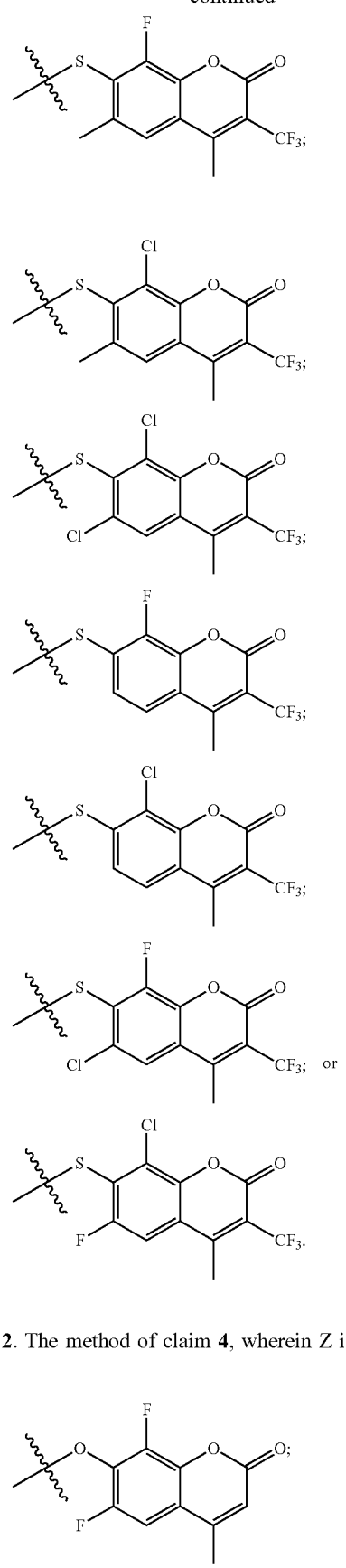
12. The method of claim 4, wherein Z is selected from:
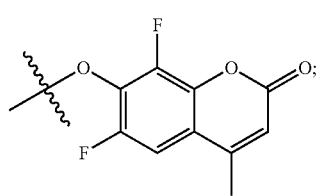

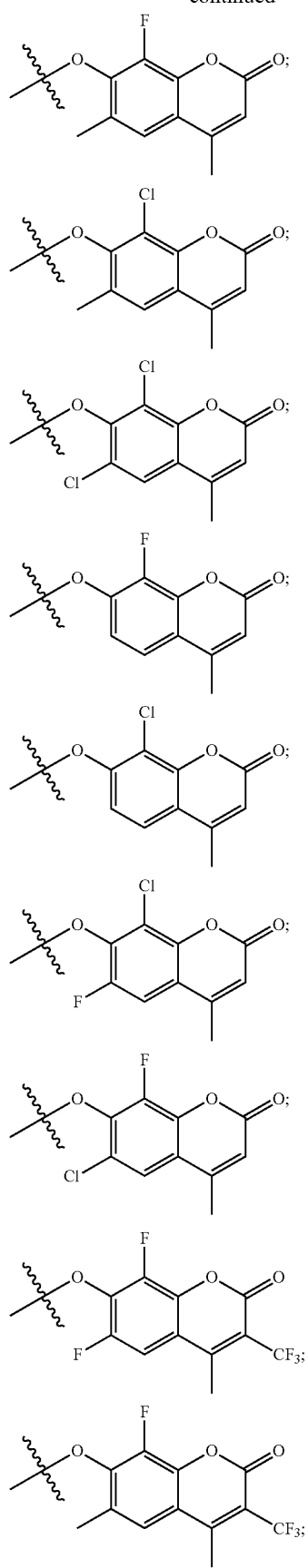
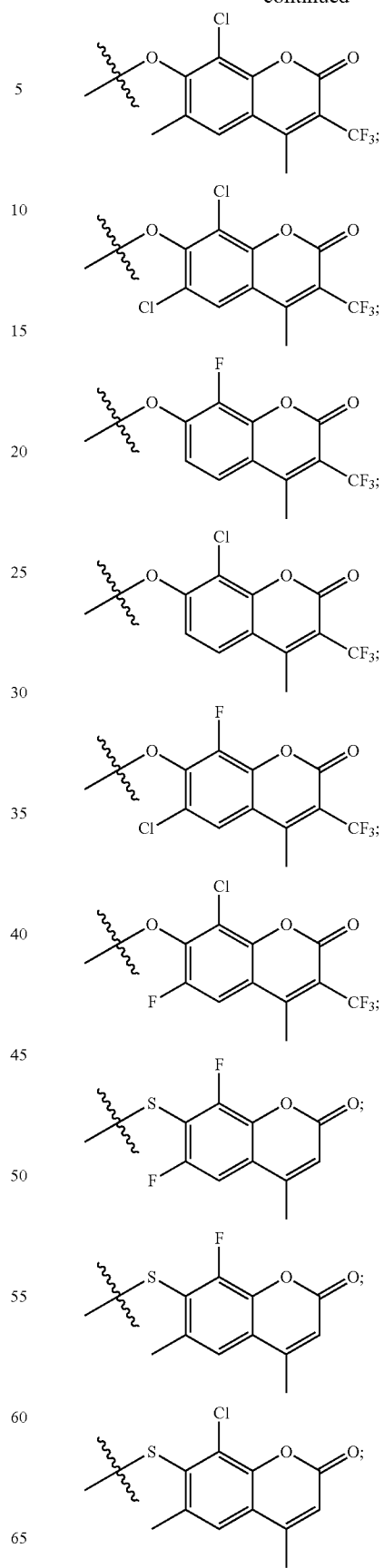

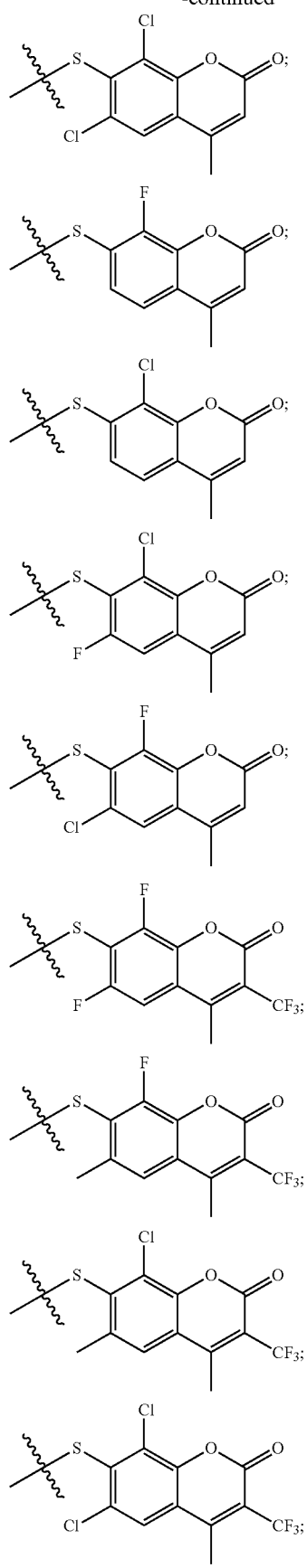
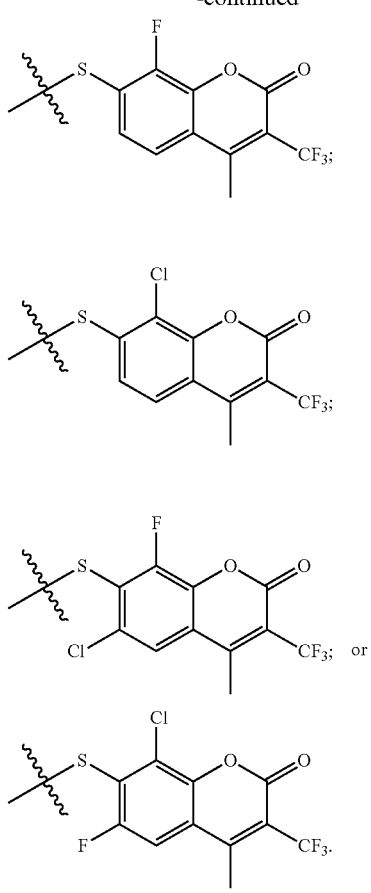
13. The method of claim 1, wherein the compound is selected from one or more of:
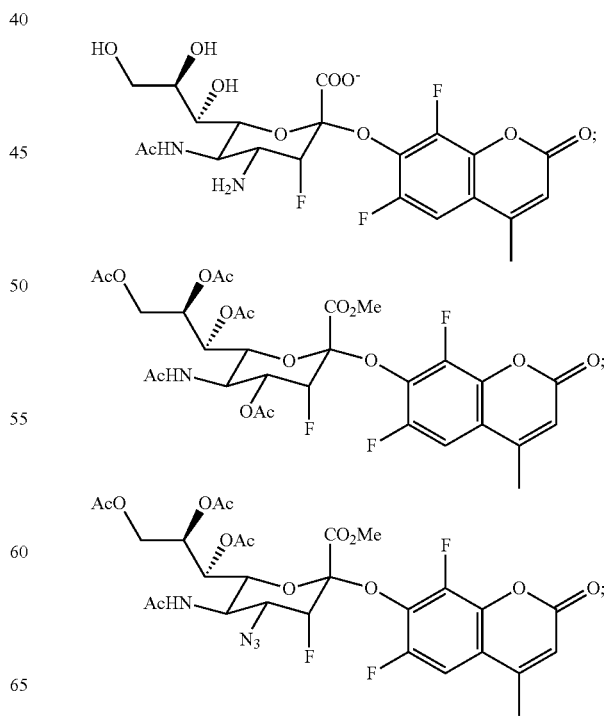

-continued
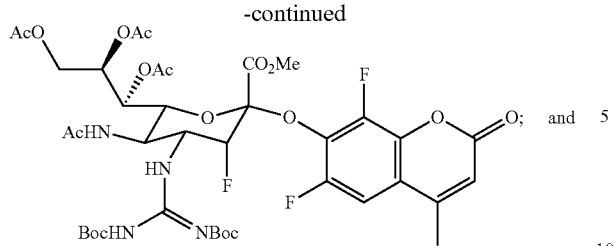
and
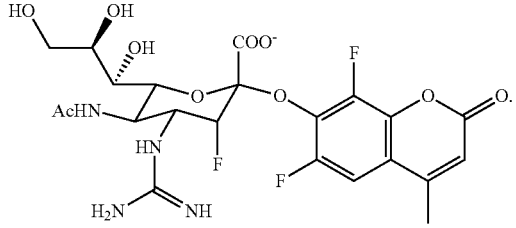
* * * * *